United States Patent
Chu et al.

(10) Patent No.: US 11,836,614 B2
(45) Date of Patent: Dec. 5, 2023

(54) IMAGE DRIVEN QUALITY CONTROL FOR ARRAY-BASED PCR

(71) Applicant: LIFE TECHNOLOGIES CORPORATION, Carlsbad, CA (US)

(72) Inventors: Yong Chu, Castro Valley, CA (US); Nivedita Majumbar, San Bruno, CA (US); Manjula Aliminati, Santa Clara, CA (US); Yongzhi Chen, Sunnyvale, CA (US); Kevin Papenfuss, Hudson, NH (US)

(73) Assignee: LIFE TECHNOLOGIES CORPORATION, Carlsbad, CA (US)

(*) Notice: Subject to any disclaimer, the term of this patent is extended or adjusted under 35 U.S.C. 154(b) by 1044 days.

(21) Appl. No.: 16/555,803

(22) Filed: Aug. 29, 2019

(65) Prior Publication Data

US 2020/0074303 A1  Mar. 5, 2020

Related U.S. Application Data

(60) Provisional application No. 62/725,894, filed on Aug. 31, 2018.

(51) Int. Cl.

| | |
|---|---|
| *G06N 3/08* | (2023.01) |
| *C12Q 1/686* | (2018.01) |
| *G06V 10/82* | (2022.01) |
| *G06N 3/044* | (2023.01) |
| *G06N 3/045* | (2023.01) |
| *G06N 3/02* | (2006.01) |

(52) U.S. Cl.
CPC ............ *G06N 3/08* (2013.01); *C12Q 1/686* (2013.01); *G06N 3/044* (2023.01); *G06N 3/045* (2023.01); *G06V 10/82* (2022.01); *G06N 3/02* (2013.01)

(58) Field of Classification Search
None
See application file for complete search history.

(56) References Cited

U.S. PATENT DOCUMENTS

| | | | |
|---|---|---|---|
| 2016/0228876 A1 | 8/2016 | Chu et al. | |
| 2017/0175169 A1 | 6/2017 | Lee et al. | |
| 2018/0156734 A1* | 6/2018 | Blanch | G01J 3/0208 |
| 2019/0164312 A1* | 5/2019 | Sunkavalli | G06T 7/97 |
| 2020/0042888 A1* | 2/2020 | Yu | G06N 3/0635 |
| 2020/0053249 A1* | 2/2020 | Perone | G06V 10/454 |

FOREIGN PATENT DOCUMENTS

| | | |
|---|---|---|
| CN | 108242054 A | 7/2018 |

OTHER PUBLICATIONS

Applied Biosystems OpenArray® Real-Time PCR System User Guide (Year: 2010).*
Anonymous., "Introduction to Quantitative PCR", Jan. 1, 2007, pp. 1-65, XP055649333, Retrieved from the Internet: URL:https://wiki.qcbs.ca/_media/stratagene_introduction_to_quantitative_pcr_methods_and_application_guide.pdf [retrieved on Dec. 4, 2019].
PCT/US2019/048862, Search Report and Written Opinion, dated Dec. 13, 2019.
Wang, T. et al., "A Fast and Robust Convolutional Neural Network-Based Defect Detection Model in Product Quality Control", The International Journal of Advanced Manufacturing Technology, Springer, London, vol. 94, No. 9, Aug. 15, 2017, pp. 3465-3471, XP036432221, ISSN: 0268-3768, DOI: 10.1007/S00170-017-0882-0 [retrieved on Aug. 15, 2017].

* cited by examiner

*Primary Examiner* — Samuel C Woolwine
(74) *Attorney, Agent, or Firm* — François A. Pelaez

(57) ABSTRACT

A system and methods are provided for image driven quality control for array based PCR. The system comprises a PCR unit, a reaction array plate, a convolutional neural network (CNN) configured to receive a sequence of images of the reaction array plate in the PCR system, and an output of the CNN coupled to a control for the reaction array plate. The method comprises applying a sequence of images from a plurality of subarrays of the reaction array plate to a plurality of CNNs during operation of the PCR system on the reaction plate array, operating the CNNs to generate failure mode predictions for the reaction plate based on the sequence of images, and coupling an output of the CNNs to one or more of a setting for manufacture of the reaction array plate or to control the PCR system.

14 Claims, 17 Drawing Sheets

|  | PASSING | BRIGHT ROX | ROX SPOTTING | ROX STRIPPING | STOP POINT BRIDGING | REFORMATTING |
|---|---|---|---|---|---|---|
| PASSING | 1166 | 0 | 53 | 0 | 19 | 1 |
| BRIGHT ROX | 1 | 5 | 7 | 0 | 1 | 1 |
| ROX SPOTTING | 51 | 0 | 878 | 1 | 6 | 3 |
| ROX STRIPPING | 2 | 0 | 19 | 23 | 0 | 0 |
| STOP POINT BRIDGING | 16 | 0 | 14 | 0 | 161 | 0 |
| REFORMATTING | 0 | 0 | 6 | 0 | 0 | 71 |

ANNOTATED (rows) / PREDICTED (columns)

FIG. 11

IMAGE DRIVEN QUALITY CONTROL FOR ARRAY-BASED PCR

CROSS-REFERENCE TO RELATED APPLICATIONS

This application claims the benefit of priority to U.S. Provisional Patent Application No. 62/725,894, filed Aug. 31, 2018, which disclosure is herein incorporated by reference in its entirety.

BACKGROUND

Deep learning is large deep neural network trained with a large amount data to learn complex and abstract patterns directly from unstructured raw data. Traditional machine learning algorithms relies heavily on hand-crafted features, which are task specific and designed by engineers with extensive domain expertise. In contrast, deep learning has a great capability to discover effective features from raw data directly and to learn complex features by combining simpler features. Deep learning has already demonstrated state-of-the-art performance in various fields such as image classification, computer vision, speech recognition, natural language processing (NLP) and medical image diagnosis et cetera. For example, Google and Microsoft have applied Convolution Neural Network (CNN) on ImageNet image classification tasks and reported 4.9% and 4.6% error rate, which beat human on image classification.

Currently, the manufacturing quality control for assay reactions plates, e.g., those utilized to carry out Polymerase Chain Reactions (PCR), perform manual visual checks on reformatting and quality control (QC) images to identify problems and determine the root cause of failures in the manufacture of assay reaction plates. However, it is a time-consuming, error prone, and tedious job for humans to visually check images during the manufacture process. It also limits production capacity and often delays the delivery of reaction plate array products to customers.

Some PCR systems are designed for maximum throughput, which may simultaneously run up to four 3,072-reaction plates in about four hours. Such systems and reaction plates often utilize mere nanoliters of sample volumes, requiring specialized instruments with complex workflows to load samples and assays onto the plate arrays. The complex workflows and the challenging use of consumables can affect the array reaction quality by lowering sensitivity and accuracy. Another side effect of this complexity is a lower array manufacturing yield. Array manufacturing failures related to sheet coating, reformatting, or sample loading are common. For example, array plates running PCR may have certain loading related artifacts including but not limited to:

1. Bridging—where fluid overflow around some adjacent reaction units and form bridges between them compromising the integrity of the reaction;
2. Leaking—the sealing unit for the reaction plate may be broken, which causing fluid to escape into an outer chamber; and
3. Assay spotting issues—for pre-spotted assay formats, some reaction units may not be loaded with the assay.

These sheet coating, reformatting or sample loading problems may be detected by visually checking reformatting and quality control (QC) images. Therefore, it is very important to automatically identify problems from QC images and quickly determine the root cause of failures during manufacture process. As PCR reactions may show anomalous behaviors such as sample loading problems in the images taken prior, during, or after the running of PCR for OpenArray or other array-based PCR platforms, it is desirable to automatically detect these types of failure modes in the customer facing software and make the troubleshooting step much more efficient and easier for customers.

SUMMARY

The present system utilizes a deep neural network, such as a convolutional neural network (CNN), to detect abnormalities in array plate reformatting and QC images to identify failure modes. The QC images, including both passing and failing sheets over a set period of time, are retrieved from a manufacturing data server. The data is classified based on passing or different failure modes. As each QC image may have more than one failure mode associated to one or multiple subarrays, the QC image is divided into (for example 48) subarray images and each subarray is annotated into passing or five failure modes including: Bright Rox, Rox Spotting, Rox Stripping, Stop Point Bridging, and Reformatting error. The annotated subarray images are used to train, evaluate and test CNN model. The trained and verified model may then be used to recognize failures and their modes in array plate reformatting and QC images.

Convolutional neural networks (CNNs) are particularly well suited to classifying features in data sets modelled in two or three dimensions. This makes CNNs popular for image classification, because images can be represented in computer memories in three dimensions (two dimensions for width and height, and a third dimension for pixel features like color components and intensity). For example a color JEG image of size 480×480 pixels can be modelled in computer memory using an array that is 480×480×3, where each of the values of the third dimension is a red, green, or blue color component intensity for the pixel ranging from 0 to 255. Inputting this array of numbers to a trained CNN will generate outputs that describe the probability of the image being a certain class (0.80 for cat, 0.15 for dog, 0.05 for bird, etc.). Image classification is the task of taking an input image and outputting a class (a cat, dog, etc.) or a probability of classes that best describes the image.

Fundamentally, CNNs input the data set, pass it through a series of convolutional transformations, nonlinear activation functions (e.g., RELU), and pooling operations (downsampling, e.g., maxpool), and an output layer (e.g., softmax) to generate the classifications.

BRIEF DESCRIPTION OF THE DRAWINGS

To easily identify the discussion of any particular element or act, the most significant digit or digits in a reference number refer to the figure number in which that element is first introduced.

FIG. 11 illustrates a validation results 1100 in accordance with one embodiment.

DETAILED DESCRIPTION

Figure 1:
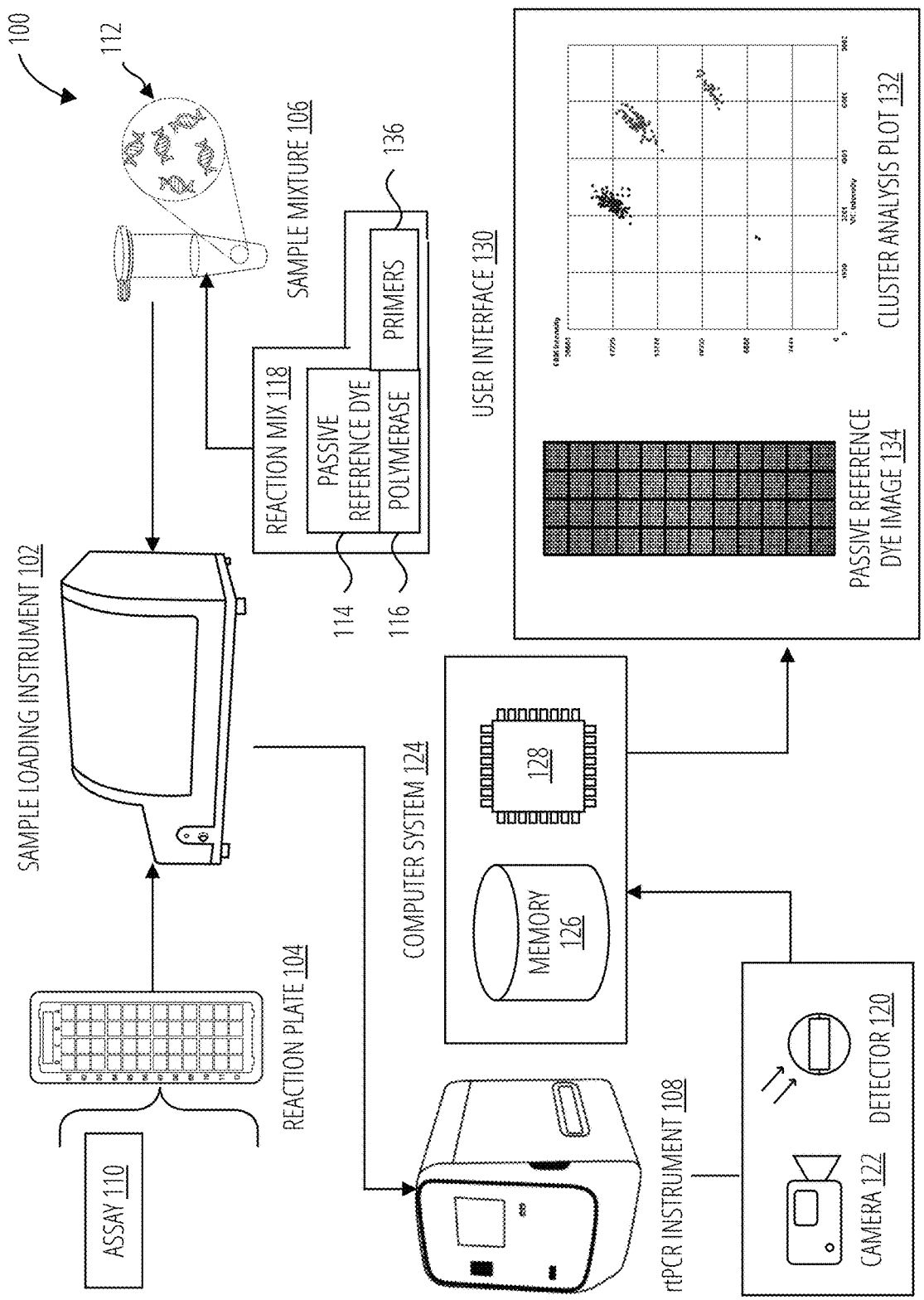
FIG. 1 illustrates a qPCR system 100 in accordance with one embodiment.

The loading problems discussed in the background for PCR assay arrays may be detected by an evaluation of the images taken prior, during or after the running of PCR reaction. Convolutional neural networks (CNNs) are trained and applied to recognize the failure modes and identify the unknown (unclassified) failure modes based on training with data for PCR runs without anomalies.

In comparison to traditional methods for troubleshooting that rely on human identification of features indicative of failure modes, the CNNs provide improved sensitivity and specificity, and can learn to recognize previously unclassified issues. Single or multiple CNNs may be applied in series or in parallel. In some embodiments, recurrent neural networks (RNNs) may be applied in conjunction with CNNs.

According to one embodiment, a deep neural network and more specifically Convolutional Neural Network (CNN) may be utilized to detect abnormalities in OpenArray® reformatting and QC images to identify failure modes. OpenArray QC images may be downloaded from an OpenArray manufacturing data server, including both passing and failing sheets from previous instrument runs. The data may then be categorized based on passing or different failure modes. Since each QC image may contain more than one failure mode associated to one or multiple subarrays, the process may divide the QC image into (for example) 48 subarray images and annotate each subarray into either passing, or one or more of five failure modes including: Bright Rox, Rox Spotting, Rox Stripping, Stop Point Bridging and Reformatting error. The annotated subarray images are used to train, evaluate and test a CNN model. The trained and verified model may then be utilized to recognize failures and their modes in OpenArray reformatting and QC images.

In one embodiment, the process of operating the deep learning neural network to identify failure modes may involve:

4. Downloading array quality control (QC) images of passing and failing plates from a manufacturing data server.
5. For each QC image, find all through-hole (reaction unit) centers in the array using a spot finding algorithm and divide the whole array image into 48 subarray images based on the identified through-hole centers.
6. Load all 48 subarray images into the annotation tool and visually inspect them and label them as passing or five failure modes including: Bright Rox, Rox Spotting, Rox Stripping, Stop Point Bridging and Reformatting error.
7. Repeat 2) and 3) for all QC images to construct the annotated training and validation datasets.
8. Use convolutional neural network with one or more hidden layers as the network to be trained.
9. Use fully connected layer as the output layer to outputs the predictions for the input subarray images.
10. Apply Softmax cross entropy cost function to calculate the loss between the predictions and the annotated labels.
11. Use Adam optimizer or other gradient descent optimizers to update the weights of the networks described above to minimize the loss against a minibatch of training samples, which are randomly selected from the training dataset, at each training step.
12. Continue the training process until the prefixed number of training steps is reached and save the trained networks for every certain training steps.
13. Evaluate the trained models, which are saved during training process, by an independent subset of subarray images in the validation dataset, which are not included in the training process. Select the trained models with minimum evaluation loss or error rate as the best trained models.
14. For a new QC image with identified through-holes centers, divide the whole array image into some number (e.g., 48) subarray images. Apply the selected trained model on those subarray images to predict passing or failure. The array QC is passing if all subarray images are good, otherwise, the array QC is failed. The system can also predict which one or more subarray is failed and which failure mode.
15. Data augmentation techniques such as adding noise, rotation, translational offsets, brightness or contrast variation or simulated subarray images by Generative Adversarial Nets (GANs) can be used to improve the robustness of the trained model.
16. During the training, the techniques such as drop-out or weight decay can be used to improve the generality of the trained model.

FIG. 1 illustrates a qPCR system 100 comprising a reaction plate 104, a sample loading instrument 102, a real-time PCR instrument 108, a sample mixture 106, a computer system 124, and a user interface 130. The reaction plate 104 comprises a plurality of subarrays each comprising a plurality of through holes that serve as the reaction location for a qPCR experiment. Each of the through-holes may be coated with an assay 110. In some configurations, the assay 110 is a probe that specifically targets a nucleotide sequence in the sample DNA. During the amplification of the sample DNA, the probe indicates its presence of the target sequence through the release of a reporter dye that is detected by the real-time PCR instrument 108. The reaction plate 104 is combined with the target polynucleotide sequences 112 in a sample loading instrument 102. Prior to combining the reaction plate 104 with the target polynucleotide sequences 112, the target polynucleotide sequences 112 are prepared in a sample mixture 106 comprising a reaction mix 118. The reaction mix 118 comprises, at least, polymerase 116, primers 136, and a passive reference dye 114. The polymerase 116 amplifies the doubled stranded DNA during the PCR reaction. The sample loading instrument 102 loads a specific volume of the sample mixture 106 into each intended through-hole in the reaction plate 104. When the sample loading instrument 102 has completed its preparation of the reaction plate 104, the reaction plate 104 is loaded into the real-time PCR instrument 108. The real-time PCR instrument 108 includes a thermocycler that cycles through different temperatures ranges that triggers specific phases for DNA replication. The first phase is high temperature phase that denature of the double stranded DNA. The next phase anneals the primers and polymerase to locations near the target polynucleotide sequences 112. and allows the assay 110 to hybridize with the target polynucleotide sequences 112. The third phase is the elongation/replication phase where the polymerase begins replicating the DNA strand. During the replication phase, the polymerase 116 may encounter the hybridized assay 110 and the target polynucleotide sequences 112. When the polymerase 116 encounters the assay 110, the reporter dye of the assay 110 is cleaved resulting a fluorescent signal being observed in the through hole. The real-time PCR instrument 108 comprises a detector 120 that detects the reporter dye from each of the through-holes during the replication process. The detected signals are reported to a computer system 124 comprising a memory 126 and a processor 128 that stores and processes the information to generate a cluster analysis plot 132 showing the copy number and instances of the target sequences in the sample mixture 106. The real-time PCR instrument 108 additionally comprises a camera 122 that captures a passive reference dye image 134. The passive reference dye image 134 may be utilized as a qualitative indication of the successful loading of the reaction plate 104 by the sample loading instrument 102 as well as provide insight into any anomalous results from in the cluster analysis plot 132. Both the cluster analysis plot 132 and the passive reference dye image 134 may be displayable through the user interface 130.

As one of ordinary skill in the art is apprised, a PCR analysis is performed on a thermal cycling instrument, which has various protocols for cycling though a plurality of thermal cycles in order to amplify a gene target. In various embodiments of the present teachings, the number of cycles performed for the amplification may be between about 20-40 cycles. For various embodiments of the present teachings, the number of cycles performed for the amplification may be greater than 40 cycles. For amplification of a gene target a thermal cycling instrument may perform a first thermal cycle of a PCR experiment in a certain cycle time that may be associated with a first thermal cycle number.

In various embodiments of a genotyping analysis, two or more DNA samples are probed with a first probe and a second probe. A processor may receive from a qPCR instrument based on any of a variety of protocols for data collection, a first data set at a first time that includes for each of the two or more DNA samples a first probe intensity and a second probe intensity at the first time. A processor may receive from a qPCR instrument based on any of a variety of protocols for data collection, a second data set at a second time that includes for each of the two or more DNA samples a first probe intensity and a second probe intensity at the second time.

According to various embodiments of the present teachings, a user interface may present to an end user a visualization tool for the analysis of the data sets received a first time and a second time. As previously mentioned, a plurality of samples may be processed for genotyping analysis in a batch, yielding data-intense data sets. Various embodiments of a systems and methods according to the present teachings provide for embodiments of a visualization tool that may assist an end user in the evaluation and analysis of such data-intense data sets. For various embodiments of systems and methods according to the present teachings, in response to input from an end user, a processor may generate a first plot of first probe intensity versus a second probe intensity using the first data set. Further, a processor may generate a second plot of first probe intensity as a function of second probe intensity using the second data set in response to input from an end user. According to various embodiments of systems and methods of the present teachings, a processor may display the first plot and the second plot in response to input from an end user. In various embodiments, the input may be an interactive process with a user interface to display the data in a step-wise fashion. In such embodiments, an end user may select any data set in any order for display.

In various embodiments, a processor may receive data during the run time of a PCR experiment. For example, a processor may receive the first data set from a qPCR instrument after the collection of the first data set and before collection of the second data set. Further, this protocol may be extended throughout the run time, so that, for example, a processor may receive the second data set from a qPCR instrument after the collection of the second data set and before collection of a subsequent data set.

In some embodiments, a processor may receive the first data set and the second data set from a qPCR instrument after thermal cycling has completed. For example, a processor may receive the first data set and the second data set after it has been stored on a computer-readable medium.

In some configurations, a visualization tool may assist an end user in the displaying of various aspects of genotyping data sets, thereby facilitating in the analysis of genotyping data. In various embodiments, a processor may display a plot showing trajectory lines between the second data set and the first data set. In various embodiments, a processor may display on the first plot quality values for the first data set and displays on the second plot quality values for the second data set. According to various embodiments, a user interface provides an interaction between selections made on a sample table and dynamically displayed on a plot of genotyping data. In various embodiments, selections made by an end user from a user interface of a visualization tool may, for example, but not limited by, provide dynamic analysis for enabling an end user to, for example, but not limited by, troubleshoot ambiguous end-point data, make manual calls, use trajectory lines to assist in visualizing clusters to enhance genotype assignment, optimize assay conditions (i.e. labeling probe, assay buffer, etc.) and optimize analysis conditions.

Various embodiments, the system utilize data sets that may be represented, for example, but not limited by, according to the graph depicted in the cluster analysis plot 132. Such a representation may arise from analyses utilizing two dyes having emissions at different wavelengths, which dyes can be associated with each of a labeling probe directed at one of two alleles for a genomic locus in a biological sample. In such duplex reactions, a discrete set of signals for each of three possible genotypes is produced. In a Cartesian coordinate system of signal 2 versus signal 1, as shown in the cluster analysis plot, each data point shown on such a graphic representation may have coordinates in one of three discrete sets of signals given. Accordingly, for each data point, a discrete set of signals for a plurality of samples may be stored as data points in a data set. Such data sets may be stored in a variety of computer readable media, and analyzed either dynamically during analysis or post analysis, as will be discussed in more detail subsequently.

One such type of assay used to demonstrate the features of embodiments of methods and systems for the visualization of genotyping data can utilize TaqMan® reagents, and may use, for example, but not limited by, FAM and VIC dye labels, as will be discussed subsequently. However, one of ordinary skill in the art will recognize that a variety of assays including labeling probe reagents may be utilized to produce data that may be analyzed according to various embodiments of methods and systems of the present teachings.

The term "labeling probe" generally, according to various embodiments, refers to a molecule used in an amplification reaction, typically for quantitative or qPCR analysis, as well as end-point analysis. Such labeling probes may be used to monitor the amplification of the target polynucleotide. In some embodiments, oligonucleotide labeling probes present in an amplification reaction are suitable for monitoring the amount of amplicon(s) produced as a function of time. Such oligonucleotide labeling probes include, but are not limited to, the 5'-exonuclease assay TaqMan® labeling probes described herein (see also U.S. Pat. No. 5,538,848), various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET labeling probes (see, e.g., U.S. Pat. No. 6,150,097), Sunrise®/Amplifluor® labeling probes (U.S. Pat. No. 6,548,250), stem-loop and duplex Scorpion™ labeling probes (Solinas et al., 2001, Nucleic Acids Research 29:E96 and U.S. Pat. No. 6,589,743), bulge loop labeling probes (U.S. Pat. No. 6,590,091), pseudo knot labeling probes (U.S. Pat. No. 6,589,250), cyclicons (U.S. Pat. No. 6,383,752), MGB Eclipse™ probe (Epoch Biosciences), hairpin labeling probes (U.S. Pat. No. 6,596,490), peptide nucleic acid (PNA) light-up labeling probes, self-assembled nanoparticle labeling probes, and ferrocene-modified labeling probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Labeling probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Labeling probes can also comprise black hole quenchers (Biosearch), Iowa Black (IDT), QSY quencher (Molecular Labeling probes), and Dabsyl and Dabcel sulfonate/carboxylate Quenchers (Epoch). Labeling probes can also comprise two labeling probes, wherein for example a fluorophore is on one probe, and a quencher on the other, wherein hybridization of the two labeling probes together on a target quenches the signal, or wherein hybridization on target alters the signal signature via a change in fluorescence. Labeling probes can also comprise sulfonate derivatives of fluorescenin dyes with a sulfonic acid group instead of the carboxylate group, phosphoramidite forms of fluorescein, phosphoramidite forms of CY 5 (available for example from Amersham).

As used herein, the term "nucleic acid sample" refers to nucleic acid found in biological samples according to the present teachings. It is contemplated that samples may be collected invasively or noninvasively. The sample can be on, in, within, from or found in conjunction with a fiber, fabric, cigarette, chewing gum, adhesive material, soil or inanimate objects. "Sample" as used herein, is used in its broadest sense and refers to a sample containing a nucleic acid from which a gene target or target polynucleotide may be derived. A sample can comprise a cell, chromosomes isolated from a cell (e.g., a spread of metaphase chromosomes), genomic DNA, RNA, cDNA and the like. Samples can be of animal or vegetable origins encompassing any organism containing nucleic acid, including, but not limited to, plants, livestock, household pets, and human samples, and can be derived from a plurality of sources. These sources may include, but are not limited to, whole blood, hair, blood, urine, tissue biopsy, lymph, bone, bone marrow, tooth, amniotic fluid, hair, skin, semen, anal secretions, vaginal secretions, perspiration, saliva, buccal swabs, various environmental samples (for example, agricultural, water, and soil), research samples, purified samples, and lysed cells. It will be appreciated that nucleic acid samples containing target polynucleotide sequences can be isolated from samples using any of a variety of sample preparation procedures known in the art, for example, including the use of such procedures as mechanical force, sonication, restriction endonuclease cleavage, or any method known in the art.

The terms "target polynucleotide," "gene target" and the like as used herein are used interchangeably herein and refer to a particular nucleic acid sequence of interest. The "target" can be a polynucleotide sequence that is sought to be amplified and can exist in the presence of other nucleic acid molecules or within a larger nucleic acid molecule. The target polynucleotide can be obtained from any source, and can comprise any number of different compositional components. For example, the target can be nucleic acid (e.g. DNA or RNA). The target can be methylated, non-methylated, or both. Further, it will be appreciated that "target" used in the context of a particular nucleic acid sequence of interest additionally refers to surrogates thereof, for example amplification products, and native sequences. In some embodiments, a particular nucleic acid sequence of interest is a short DNA molecule derived from a degraded source, such as can be found in, for example, but not limited to, forensics samples. A particular nucleic acid sequence of interest of the present teachings can be derived from any of a number of organisms and sources, as recited above.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

In some embodiments, PCR amplification products may be detected by fluorescent dyes conjugated to the PCR amplification primers, for example as described in PCT patent application WO 2009/059049. PCR amplification products can also be detected by other techniques, including, but not limited to, the staining of amplification products, e.g. silver staining and the like.

In some embodiments, detecting comprises an instrument, i.e., using an automated or semi-automated detecting means that can, but needs not, comprise a computer algorithm. In some embodiments, the instrument is portable, transportable or comprises a portable component which can be inserted into a less mobile or transportable component, e.g., residing in a laboratory, hospital or other environment in which detection of amplification products is conducted. In certain embodiments, the detecting step is combined with or is a continuation of at least one amplification step, one sequencing step, one isolation step, one separating step, for example but not limited to a capillary electrophoresis instrument comprising at least one fluorescent scanner and at least one graphing, recording, or readout component; a chromatography column coupled with an absorbance monitor or fluorescence scanner and a graph recorder; a chromatography column coupled with a mass spectrometer comprising a recording and/or a detection component; a spectrophotometer instrument comprising at least one UV/visible light scanner and at least one graphing, recording, or readout component; a microarray with a data recording device such as a scanner or CCD camera; or a sequencing instrument with detection components selected from a sequencing instrument comprising at least one fluorescent scanner and at least one graphing, recording, or readout component, a sequencing by synthesis instrument comprising fluorophore-labeled, reversible-terminator nucleotides, a pyro sequencing method comprising detection of pyrophosphate (PPi) release following incorporation of a nucleotide by DNA polymerase, pair-end sequencing, polony sequencing, single molecule sequencing, nanopore sequencing, and sequencing by hybridization or by ligation as discussed in Lin, B. et al. "Recent Patents on Biomedical Engineering (2008)1(1)60-67, incorporated by reference herein.

In certain embodiments, the detecting step is combined with an amplifying step, for example but not limited to, real-time analysis such as Q-PCR. Exemplary means for performing a detecting step include the ABI PRISM® Genetic Analyzer instrument series, the ABI PRISM® DNA Analyzer instrument series, the ABI PRISM® Sequence Detection Systems instrument series, and the Applied Biosystems Real-Time PCR instrument series (all from Applied Biosystems); and microarrays and related software such as the Applied Biosystems microarray and Applied Biosystems 1700 Chemiluminescent Microarray Analyzer and other commercially available microarray and analysis systems available from Affymetrix, Agilent, and Amersham Biosciences, among others (see also Gerry et al., J. Mol. Biol. 292:251-62, 1999; De Bellis et al., Minerva Biotec 14:247-52, 2002; and Stears et al., Nat. Med. 9:140-45, including supplements, 2003) or bead array platforms (Illumina, San Diego, Calif.). Exemplary software includes GeneMapper™ Software, GeneScan® Analysis Software, and Genotyper® software (all from Applied Biosystems).

In some embodiments, an amplification product can be detected and quantified based on the mass-to-charge ratio of at least a part of the amplicon (m/z). For example, in some embodiments, a primer comprises a mass spectrometry-compatible reporter group, including without limitation, mass tags, charge tags, cleavable portions, or isotopes that are incorporated into an amplification product and can be used for mass spectrometer detection (see, e.g., Haff and Smirnov, Nucl. Acids Res. 25:3749-50, 1997; and Sauer et al., Nucl. Acids Res. 31:e63, 2003). An amplification product can be detected by mass spectrometry. In some embodiments, a primer comprises a restriction enzyme site, a cleavable portion, or the like, to facilitate release of a part of an amplification product for detection. In certain embodiments, a multiplicity of amplification products are separated by liquid chromatography or capillary electrophoresis, subjected to ESI or to MALDI, and detected by mass spectrometry. Descriptions of mass spectrometry can be found in, among other places, The Expanding Role of Mass Spectrometry in Biotechnology, Gary Siuzdak, MCC Press, 2003.

In some embodiments, detecting comprises a manual or visual readout or evaluation, or combinations thereof. In some embodiments, detecting comprises an automated or semi-automated digital or analog readout. In some embodiments, detecting comprises real-time or endpoint analysis. In some embodiments, detecting comprises a microfluidic device, including without limitation, a TaqMan® Low Density Array (Applied Biosystems). In some embodiments, detecting comprises a real-time detection instrument. Exemplary real-time instruments include, the ABI PRISM® 7000 Sequence Detection System, the ABI PRISM® 7700 Sequence Detection System, the Applied Biosystems 7300 Real-Time PCR System, the Applied Biosystems 7500 Real-Time PCR System, the Applied Biosystems 7900 HT Fast Real-Time PCR System (all from Applied Biosystems); the LightCycler™ System (Roche Molecular); the Mx3000P™ Real-Time PCR System, the Mx3005P™ Real-Time PCR System, and the Mx4000® Multiplex Quantitative PCR System (Stratagene, La Jolla, Calif.); and the Smart Cycler System (Cepheid, distributed by Fisher Scientific). Descriptions of real-time instruments can be found in, among other places, their respective manufacturer's user's manuals; McPherson; DNA Amplification: Current Technologies and Applications, Demidov and Broude, eds., Horizon Bioscience, 2004; and U.S. Pat. No. 6,814,934.

The term "amplification reaction mixture" and/or "master mix" may refer to an aqueous solution comprising the various (some or all) reagents used to amplify a target nucleic acid. Such reactions may also be performed using solid supports or semi-solid supports (e.g., an array). The reactions may also be performed in single or multiplex format as desired by the user. These reactions typically include enzymes, aqueous buffers, salts, amplification primers, target nucleic acid, and nucleoside triphosphates. In some embodiments, the amplification reaction mix and/or master mix may include one or more of, for example, a buffer (e.g., Tris), one or more salts (e.g., MgC, KCl), glycerol, dNTPs (dA, dT, dG, dC, dU), recombinant BSA (bovine serum albumin), a dye (e.g., ROX passive reference dye), one or more detergents, polyethylene glycol (PEG), polyvinyl pyrrolidone (PVP), gelatin (e.g., fish or bovine source) and/or antifoam agent. Depending upon the context, the mixture can be either a complete or incomplete amplification reaction mixture. In some embodiments, the master mix does not include amplification primers prior to use in an amplification reaction. In some embodiments, the master mix does not include target nucleic acid prior to use in an amplification reaction. In some embodiments, an amplification master mix is mixed with a target nucleic acid sample prior to contact with amplification primers.

In some embodiments, the amplification reaction mixture comprises amplification primers and a master mix. In some embodiments, the amplification reaction mixture comprises amplification primers, a detectably labeled probe, and a master mix.

In some embodiments, the reaction mixture of amplification primers and master mix or amplification primers, probe and master mix are dried in a storage vessel or reaction vessel. In some embodiments, the reaction mixture of amplification primers and master mix or amplification primers, probe and master mix are lyophilized in a storage vessel or reaction vessel. In some embodiments, the disclosure generally relates to the amplification of multiple target-specific sequences from a single control nucleic acid molecule. For example, in some embodiments that single control nucleic acid molecule can include RNA and in other embodiments, that single control nucleic acid molecule can include DNA. In some embodiments, the target-specific primers and primer pairs are target-specific sequences that can amplify specific regions of a nucleic acid molecule, for example, a control nucleic acid molecule. In some embodiments, the target-specific primers can prime reverse transcription of RNA to generate target-specific cDNA. In some embodiments, the target-specific primers can amplify target DNA or cDNA. In some embodiments, the amount of DNA required for selective amplification can be from about 1 ng to 1 microgram. In some embodiments, the amount of DNA required for selective amplification of one or more target sequences can be about 1 ng, about 5 ng or about 10 ng. In some embodiments, the amount of DNA required for selective amplification of target sequence is about 10 ng to about 200 ng.

As used herein, the term "reaction vessel" generally refers to any container, chamber, device, or assembly, in which a reaction can occur in accordance with the present teachings. In some embodiments, a reaction vessel may be a microtube, for example, but not limited to, a 0.2 mL or a 0.5 mL reaction tube such as a Micro Amp™ Optical tube (Life Technologies Corp., Carlsbad, Calif.) or a micro-centrifuge tube, or other containers of the sort in common practice in molecular biology laboratories. In some embodiments, a reaction vessel comprises a well of a multi-well plate (such as a 48-, 96-, or 384-well microtiter plate), a spot on a glass slide, a well in a TaqMan™ Array Card or a channel or chamber of a microfluidics device, including without limitation a TaqMan™ Low Density Array, or a through-hole of a TaqMan™ OpenArray™ Real-Time PCR plate (Applied Biosystems, Thermo Fisher Scientific). For example, but not as a limitation, a plurality of reaction vessels can reside on the same support. An OpenArray™ Plate, for example, is a reaction plate 3072 through-holes. Each such through-hole in such a plate may contain a single TaqMan™ assay. In some embodiments, lab-on-a-chip-like devices available, for example, from Caliper or Fluidigm can provide reaction vessels. It will be recognized that a variety of reaction vessels are commercially available or can be designed for use in the context of the present teachings.

The terms "annealing" and "hybridizing", including, without limitation, variations of the root words "hybridize" and "anneal", are used interchangeably and mean the nucleotide base—pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers and probes anneal to complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349 (1968).

In general, whether such annealing takes place is influenced by, among other things, the length of the complementary portions of the complementary portions of the primers and their corresponding binding sites in the target flanking sequences and/or amplicons, or the corresponding complementary portions of a reporter probe and its binding site; the pH; the temperature; the presence of mono- and divalent cations; the proportion of G and C nucleotides in the hybridizing region; the viscosity of the medium; and the presence of denaturants. Such variables influence the time required for hybridization. Thus, the preferred annealing conditions will depend upon the particular application. Such conditions, however, can be routinely determined by persons of ordinary skill in the art, without undue experimentation. Preferably, annealing conditions are selected to allow the primers and/or probes to selectively hybridize with a complementary sequence in the corresponding target flanking sequence or amplicon, but not hybridize to any significant degree to different target nucleic acids or non-target sequences in the reaction composition at the second reaction temperature.

Figure 2:
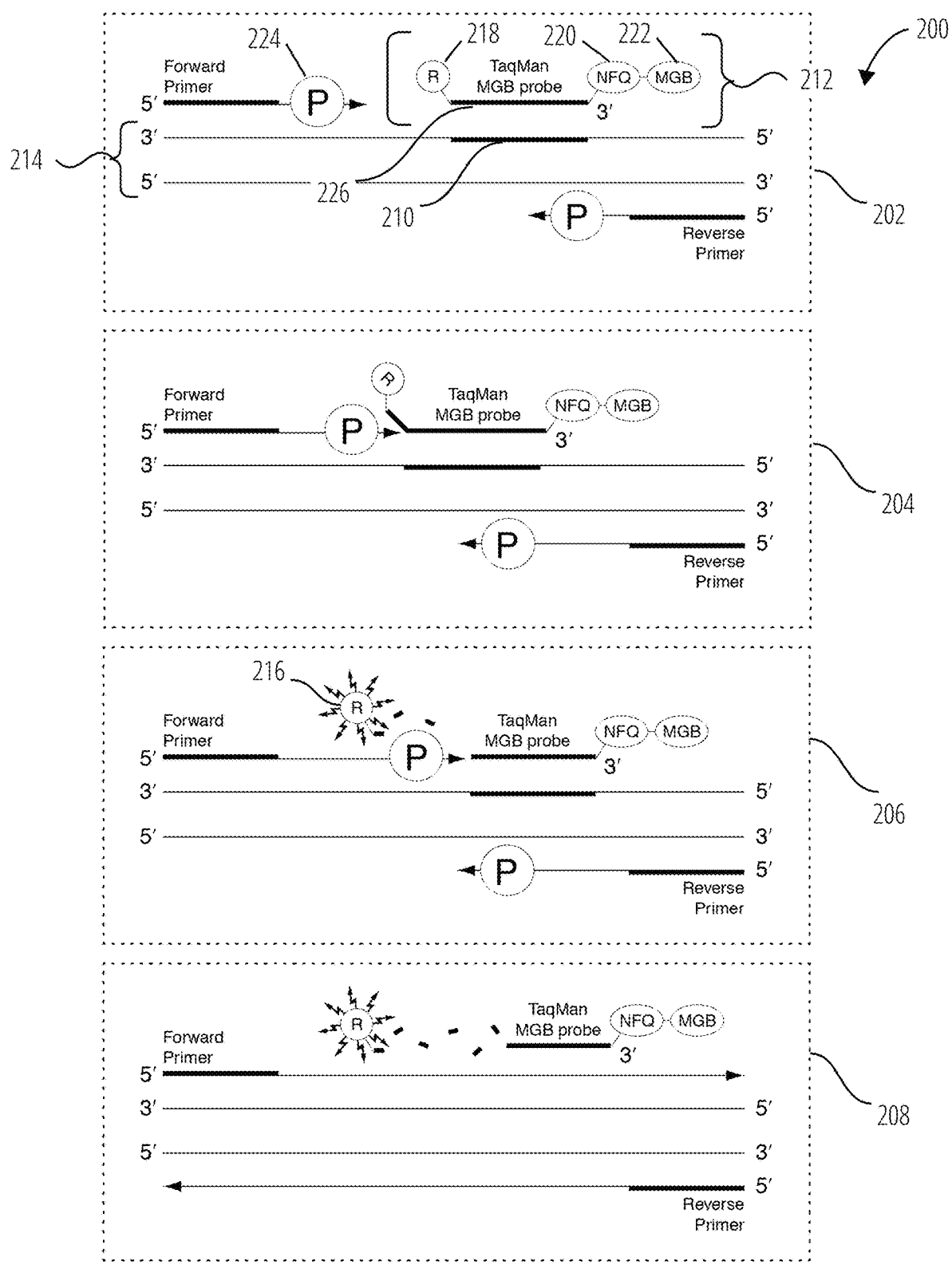
FIG. 2 illustrates a process 200 in accordance with one embodiment.

FIG. 2 illustrates a process 200 in accordance with one embodiment utilized in PCR amplification, specifically a 5' nuclease assay utilized in PCR amplification. The process 200 shows four stages of this assay process that occurs in every cycle and does not interfere with the exponential accumulation of product. The four stages include a polymerization phase 202, a strand displacement phase 204, a cleavage phase 206, and a completion phase 208. During the polymerization phase 202 a forward primer and a reverse primer start replicating a section of a double stranded DNA 214 near a target sequence 210. The forwards primer (5'->3') comprises a hot-start polymerase 224 (Taq polymerase), that functions at temperatures that DNA polymerase is inactive avoiding unwanted replication. A probe 212 comprises a reporter dye 218, a complementary sequence 226, a non-fluorescent quencher 220, and a minor groove binder 222. The probe 212 hybridizes to a target sequence 210 through the complementary sequence 226. The non-fluorescent quencher 220 and the minor groove binder 222 function as molecules are attached to the 3' end of probe 212. When the probe is intact, the non-fluorescent quencher 220 (NFQ) prevents the reporter dye 218 from emitting a fluorescence signal. Because the non-fluorescent quencher 220 does not fluoresce, it produces lower background signals, resulting in improved precision in quantification. The minor groove binder 222 (MGB) increases the melting temperature (Tm) of the probe without increasing its length, allowing for the design of shorter probes. During the polymerization phase 202, the hot-start polymerase 224 moves towards the probe 212 with the reporter dye 218 attached to the 5' side of the probe 212.

In the strand displacement phase 204 the hot-start polymerase 224 interacts with the hybridized probe 212 displacing the reporter dye 218. In cleavage phase 206, the hot-start polymerase 224 cleaves the reporter dye 218 from the probe 212. Cleavage separates the reporter dye from the quencher dye; with the non-fluorescent quencher 220 no longer block the reporter dye 218, the separated reporter dye 216 increases its fluorescence. The increase in fluorescence occurs only if the target sequence is complementary to the probe and is amplified during PCR. The instrument detects the fluorescence from the reporter dye indicating the presence of the target sequence on the double stranded DNA 214. Due to the hybridization of the probe 212 to the target sequence 210, the hot-start polymerase 224 stops at the complementary sequence 226 indicating the completion phase 208.

Figure 3:
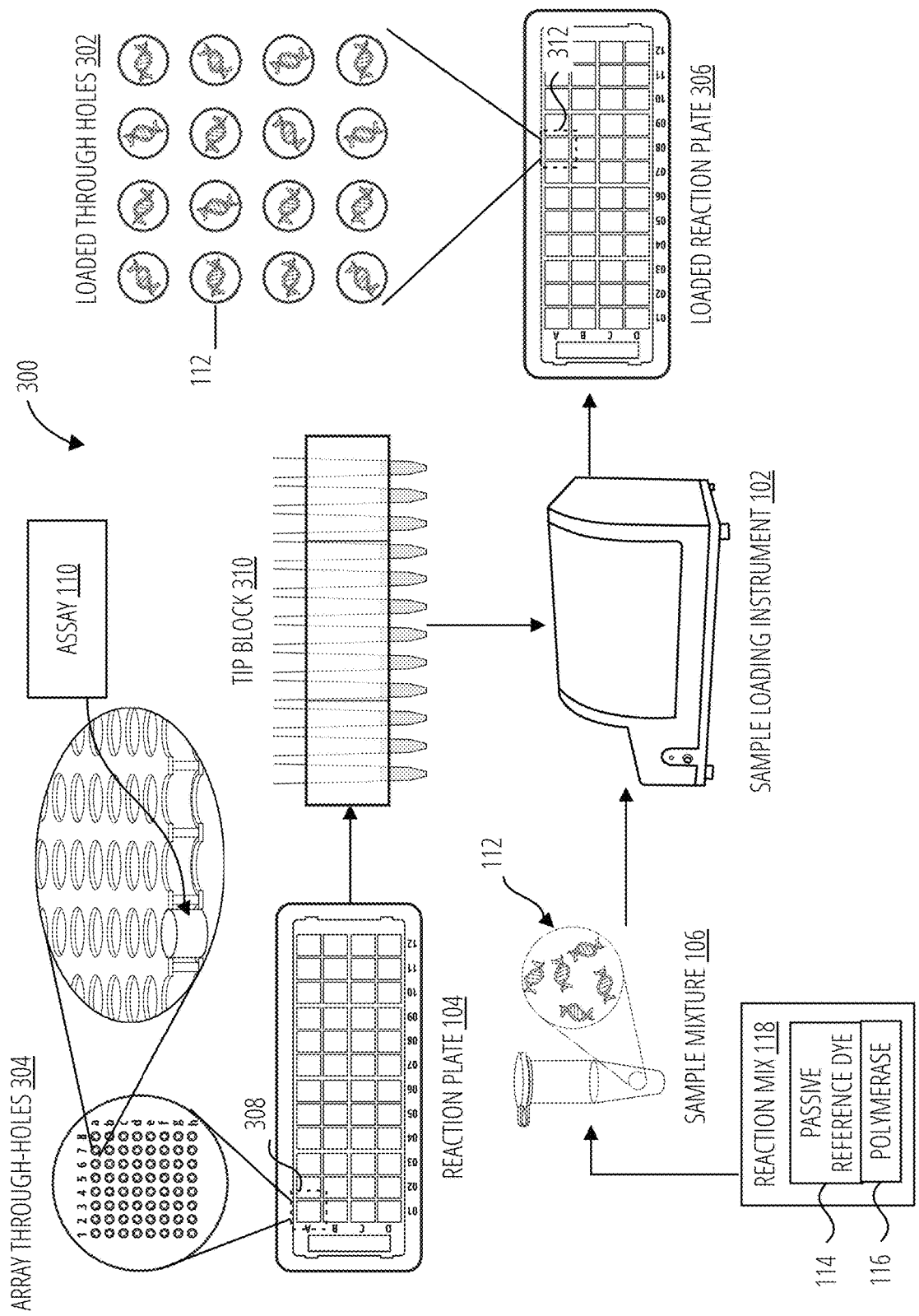
FIG. 3 illustrates a plate preparation 300 in accordance with one embodiment.

FIG. 3 illustrates plate preparation 300 for a reaction plate 104 before it is loaded into an rtPCR instrument. A reaction plate 104 comprises a plurality of sub arrays, each sub array 308 comprising a plurality of through array through-holes 304. Each through-hole may serve as a reaction location for an assay 110. In some configurations, the reaction plate 104 comprises 48 subarrays with each sub array comprising 64 through-holes each capable of holding 33-nL of reaction volume. In the aforementioned configuration, the reaction plate 104 comprises 3072 through-holes.

Depending on the configuration of the reaction plate 104, some of the array through-holes 304 will include an assay 110 spotted within them. Each through-hole comprises a hydrophilic interior where the assay 110 may be spotted. The hydrophilic through-holes are also surrounded by hydrophobic surfaces that keep the reaction contained.

To accurately load a set volume into each desired array through-holes 304, a sample loading instrument 102 is utilized. The sample loading instrument 102 aliquots a set volume of a sample mixture 106 into each desired through-hole of the reaction plate 104. In some configurations, a tip block 310 is utilized by the sample loading instrument 102 to dispense the sample mixture into the through-holes of the reaction plate 104.

When the sample loading instrument 102 is operated, the tip block 310 may move across the reaction plate 104 allowing for a set volume of the sample mixture 106 to be delivered to the specific array through-holes 304. When the sample loading instrument 102 is completed its run, the reaction plate 104 is converted into a loaded reaction plate 306 where the plurality of sub arrays, for example sub array 312, comprise loaded through holes 302 comprising the target polynucleotide sequences 112.

Figure 4:
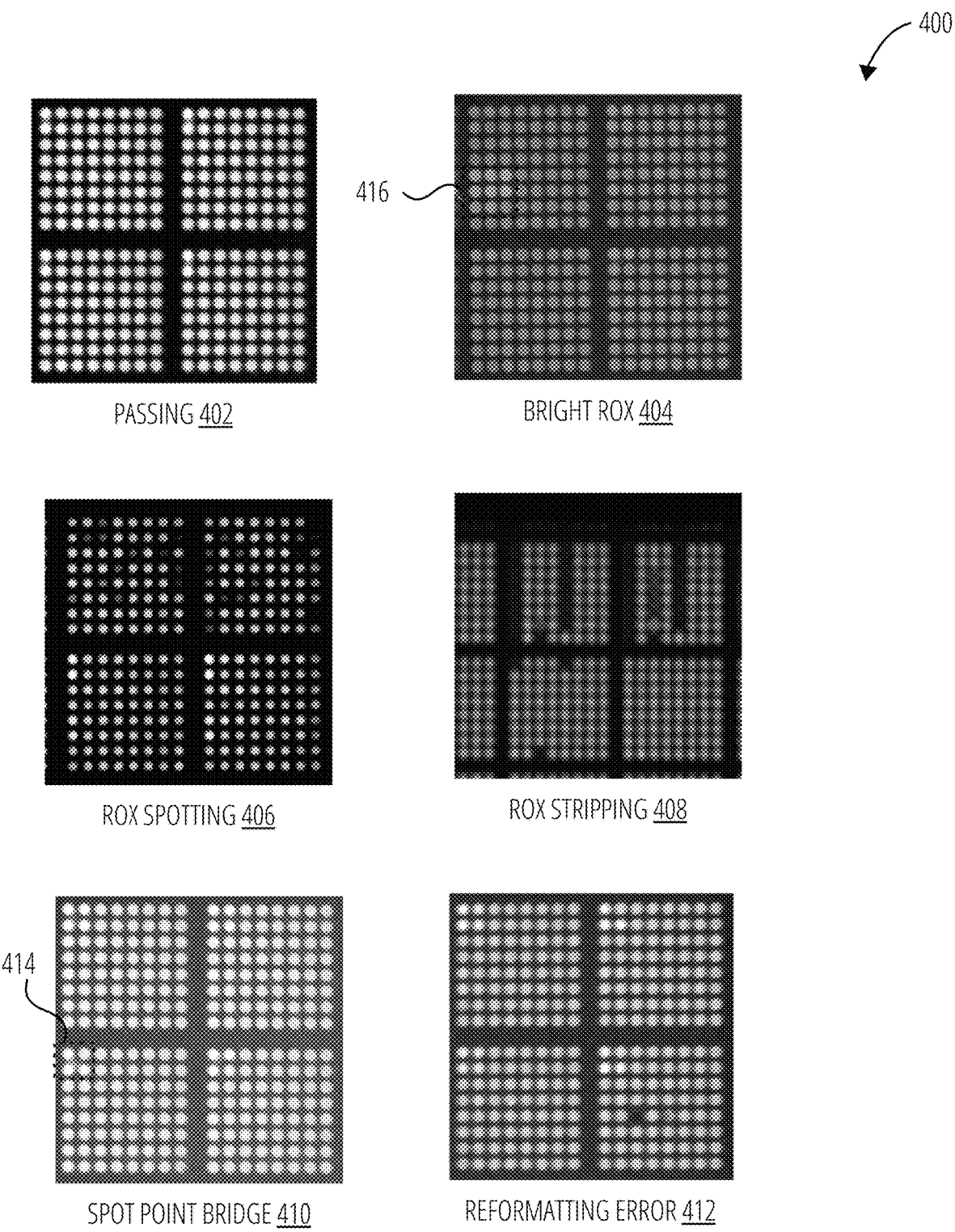
FIG. 4 illustrates a QC image conditions 400 in accordance with one embodiment.

Referencing FIG. 4, QC image conditions 400 illustrates passive reference dyes images showing characteristic flaws that lead to poor data collection. When a spotted sample plate is loaded in the rtPCR instrument, an image of the spotted plate is taken under a fluorescent light. The fluorescent light cause the passive reference dye to fluoresce indicating the presence of the sample mixture (i.e., target polynucleotides and reaction mixture) The passive reference dye images are collected and stored by a computer system associated with the instrument. The passive reference dye images may be analyzed early in the quality control process to determine if there were any errors associated with spotting the samples onto the array plate.

Image 402 illustrates a passing image showing brightly lit dots arranged in a grid pattern. Each dot represents a through-hole and a passing image shows all through-holes having similar brightness with a uniform background.

Image 404, image 406, image 408, image 410, and image 412 represent five common failure conditions associated with the spotting of the array plate. Image 404 represents one of the failing condition referred to as bright rox. The bright ROX indicates that there are bright spots 416 visible in some through-holes in comparison to other through holes. The bright spots 416 may indicate higher presence of the passive reference dye in the brighter through-holes which may indicate improper spotting of the plate. Image 406 represents ROX spotting where random through-holes appear darker than other and are distributed throughout the array plate. In some instances, the darker through-holes may indicate a partially loaded through hole. Image 408 represents ROX stripping where some darker looking through-holes are arranged on the array plate in an almost linear pattern. In some instances, the ROX stripping may indicate that the plate is not sitting tightly against the stop block on the right side of the plate holder, the autoloader is misaligned, or that there are too many bubbles and/or foam in the tip of the autoloader. In image 404, image 406, and image 408, an image is considered a fail if there are at least seven affected through-holes, but there is not an absolute cutoff as some failure identifications are subjective since the determination is based on relative brightness of the through-holes.

Image 410 represents a failure condition called a spot point bridge. A spot point bridge 414 appears as a grey "bridge" in the background area connecting a few (two or four) neighboring through-holes. A spot point bridge 414 may be caused by improper removal of the autoloader tip block which caused some of the sample mixture to spill out of the through-hole. Image 412 represents a reformatting error and is characterized by at least one random empty through-hole. The reformatting error may indicate an issue with the array plate or an issue with configuration of the array in the autoloader.

Figure 5:
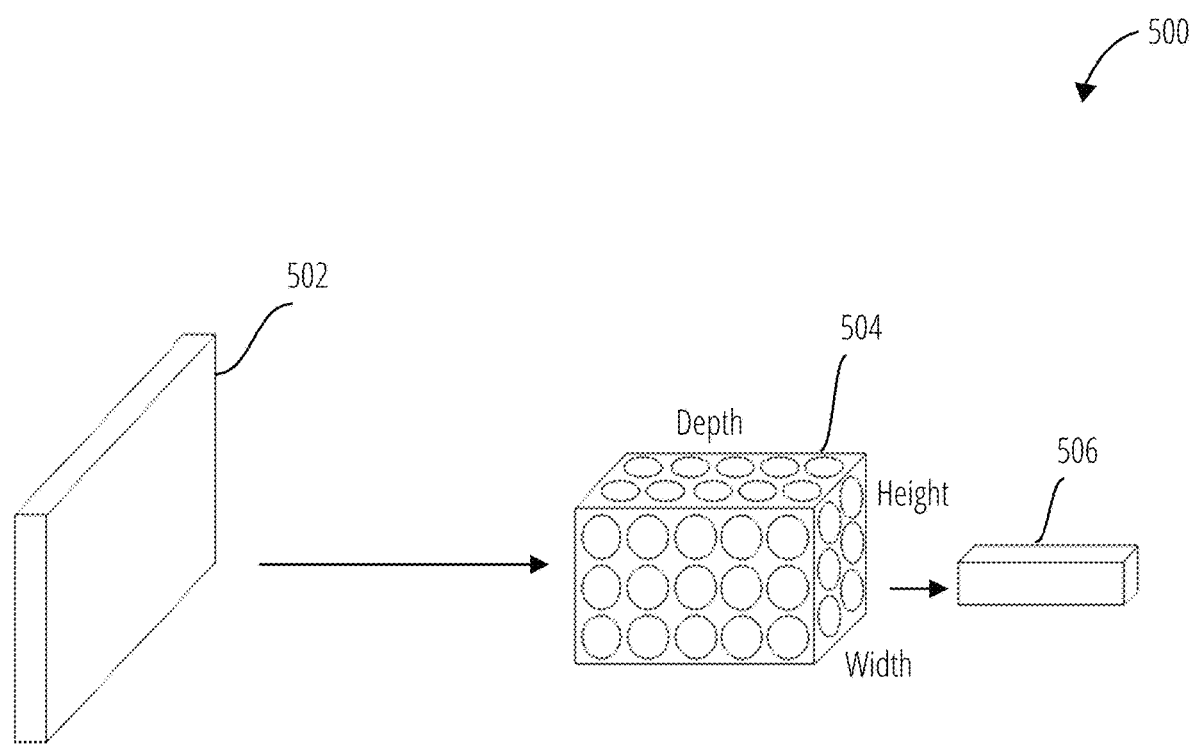
FIG. 5 illustrates a convolutional neural network 500 in accordance with one embodiment.

FIG. 5 illustrates an exemplary convolutional neural network 500. The convolutional neural network 500 arranges its neurons in three dimensions (width, height, depth), as visualized in convolutional layer 504. Every layer of the convolutional neural network 500 transforms a 3D volume of inputs to a 3D output volume of neuron activations. In this example, the input layer 502 encodes the image, so its width and height would be the dimensions of the image, and the depth would be 3 (Red, Green, Blue channels). The convolutional layer 504 further transforms the outputs of the input layer 502, and the output layer 506 transforms the outputs of the convolutional layer 504 into one or more classifications of the image content. In one embodiment, the convolutional neural network 500 may utilize one input layer 502, six hidden layers (one which one or more may be a convolutional layer 504), and an output layer 506. In addition to one or more convolutional layer 504, the convolutional neural network 500 may utilize pooling layers and fully connected layers.

Figure 6:
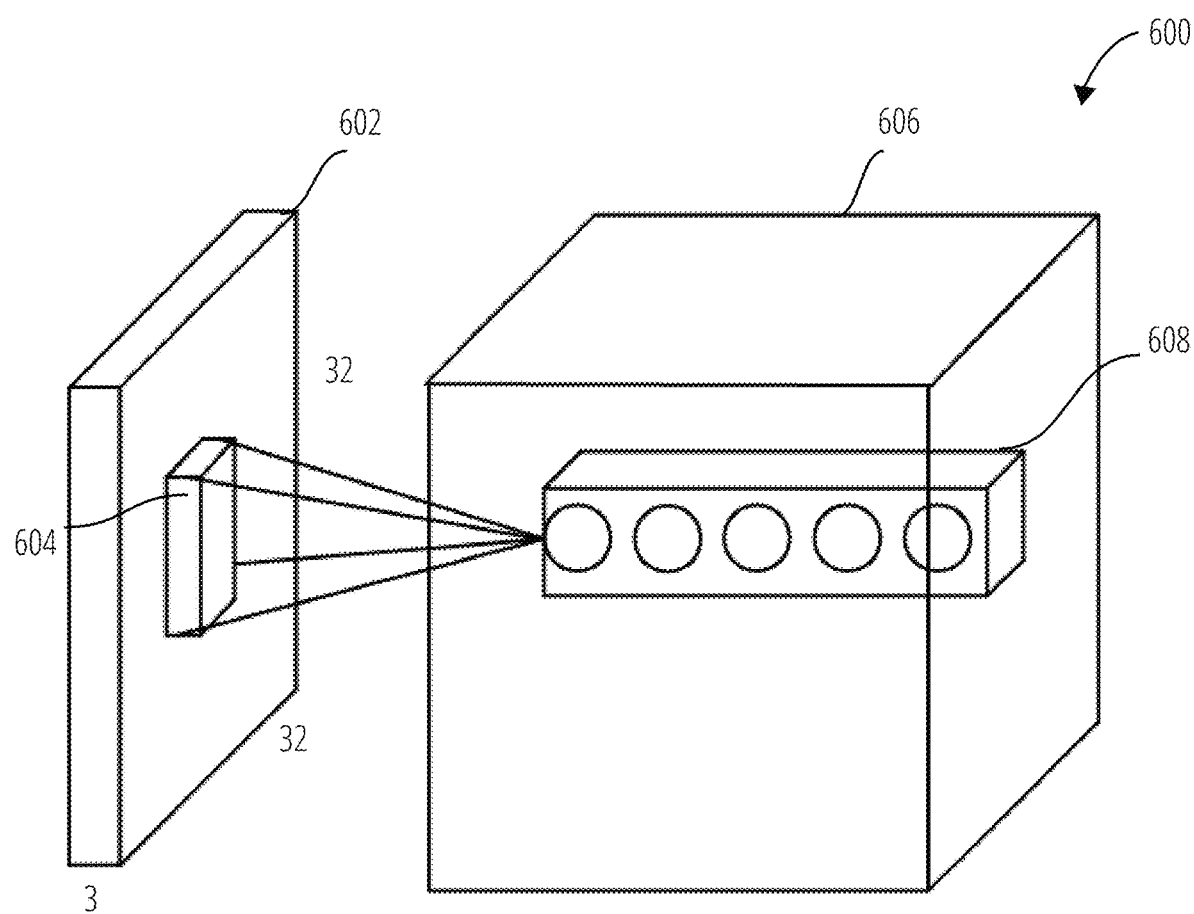
FIG. 6 illustrates a convolutional neural network layers 600 in accordance with one embodiment.

FIG. 6 illustrates an exemplary convolutional neural network layers 600 in more detail. An example subregion of the input layer region 604 of an input layer region 602 region of an image is analyzed by a set of convolutional layer subregion 608 in the convolutional layer 606. The input layer region 602 is 32×32 neurons long and wide (e.g., 32×32 pixels), and three neurons deep (e.g., three color channels per pixel). Each neuron in the convolutional layer 606 is connected only to a local region in the input layer region 602 spatially (in height and width), but to the full depth (i.e. all color channels if the input is an image). Note, there are multiple neurons (5 in this example) along the depth of the convolutional layer subregion 608 that analyzes the subregion of the input layer region 604 of the input layer region 602, in which each neuron of the convolutional layer subregion 608 may receive inputs from every neuron of the subregion of the input layer region 604.

Figure 7:
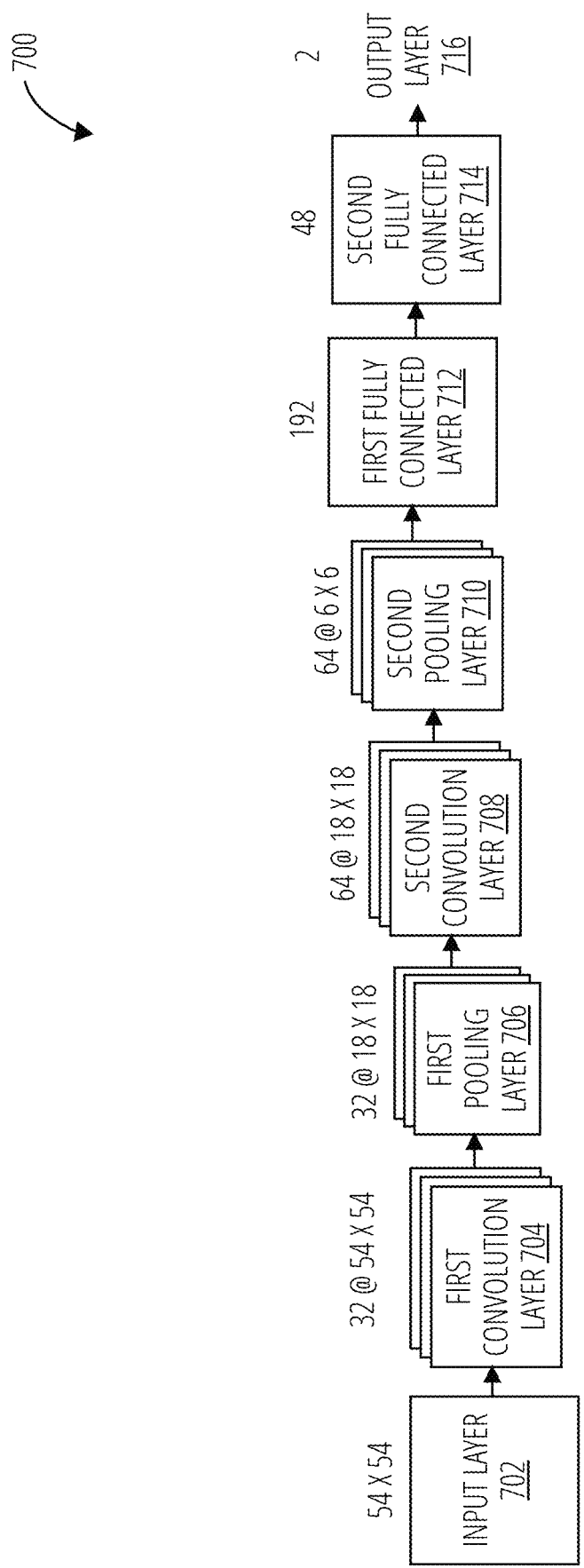
FIG. 7 illustrates a neural network 700 in accordance with one embodiment.

Referring to FIG. 7, a neural network 700 comprises an input layer 702, a first convolution layer 704, a first pooling layer 706, a second convolution layer 708, a second pooling layer 710, a first fully connected layer 712, and a second fully connected layer 714.

The input layer 702 may be a 54×54 array. The 54×54 array may be a subarray of an array plate. For example, an array plate may be arranged as a 4×12 array of subarrays. Therefore, each array plate may be divided into 48 subarrays, each of which is sent to the neural network 700 to determine whether it passed or failed. Each value in the array may be a representation of a color channel, for example an R, G, B color channel, or a black/white color scale. The input layer 702 is then convolved into the first convolution layer 704. The first convolution layer 704 comprises 32 arrays, each of which being 54×54. The first convolution layer 704 is pooled into the first pooling layer 706. The pooling function may be a maxpool function operating on a 3×3 region of the first convolution layer 704. The first pooling layer 706 may then comprise 32 arrays, each of which is 18×18. The first pooling layer 706 is then convolved into the second convolution layer 708. The second convolution layer 708 may have 64 arrays, each of which is 18×18. The second convolution layer 708 is pooled into the second pooling layer 710. The pooling function may be a maxpool function operating on a 3×3 region of the second convolution layer 708. The second pooling layer 710 may then comprise 64 arrays, each of which is 6×6. Each of the 64 6×6 arrays are sent to the first fully connected layer 712, which may have 192 nodes. The first fully connected layer 712 is then fully connected to the second fully connected layer 714, which may have 48 nodes. The output layer 716 then has two states, a pass or a fail, and is fully connected to the second fully connected layer 714. The output layer 716 may also predict a type (class) of failure.

The neural network 700 may be trained and operated by first retrieving historical QC images of passing and failing plates from a manufacturing data server. For each image, the through-hole (reaction unit) centers in the array are found by a spot finding algorithm and the whole array image is divided into 48 subarray images based on the identified through-hole centers. The 48 subarray images are loaded into the annotation tool and are inspected and labeled as passing or failing with five failure modes including: Bright Rox, Rox Spotting, Rox Stripping, Stop Point Bridging, and Reformatting error. The previous two steps are repeated for the QC images to construct the annotated training and validation datasets. A convolutional neural network with one or more hidden layers is initialized to be utilized as the network to be trained. A fully connected layer is utilized as the output layer to output the predictions for the input subarray images. A Softmax cross entropy cost function is applied to calculate the loss between the predictions and the annotated labels. An Adam optimizer or other gradient descent optimizer is utilized to update the weights of the networks described above to minimize the loss against a minibatch of training samples, which are randomly selected from the training dataset, at each training step. The training process is continued until the prefixed number of training steps is reached and save the trained networks for every certain training steps. The trained models are evaluated, which were saved during training process, by an independent subset of subarray images in the validation dataset, which are not included in the training process. The trained models with minimum evaluation loss or error rate are then selected as the best trained models. During the training, techniques, such as drop-out or weight decay, may be used to improve the generality of the trained model.

During operation, new QC image with identified through-holes centers, the whole array image is divided into 48 subarray images. The selected trained model is applied on those subarray images to predict passing or failures. The array QC may be passing if all subarray images are good, otherwise, the array QC is failed. The neural network 700 may also predict which subarray failed and by which failure mode.

Further data augmentation techniques, such as adding noise, rotation, translational offsets, brightness or contrast variation, or simulated subarray images by Generative Adversarial Nets (GANs), may be utilized to improve the robustness of the trained model.

Transfer learning is a technique to leverage multiple data sources to overcome data scarcity problem. By using transfer learning, the network already trained for a similar problem is modified and then re-trained with a fraction of the labeled data. Here, the neural network 700 may use the models learned from other image datasets, such as ImageNet data, and replace the final classification layer with a new fully connected layer to predict passing and failure modes for the array-based PCR data.

Figure 8:
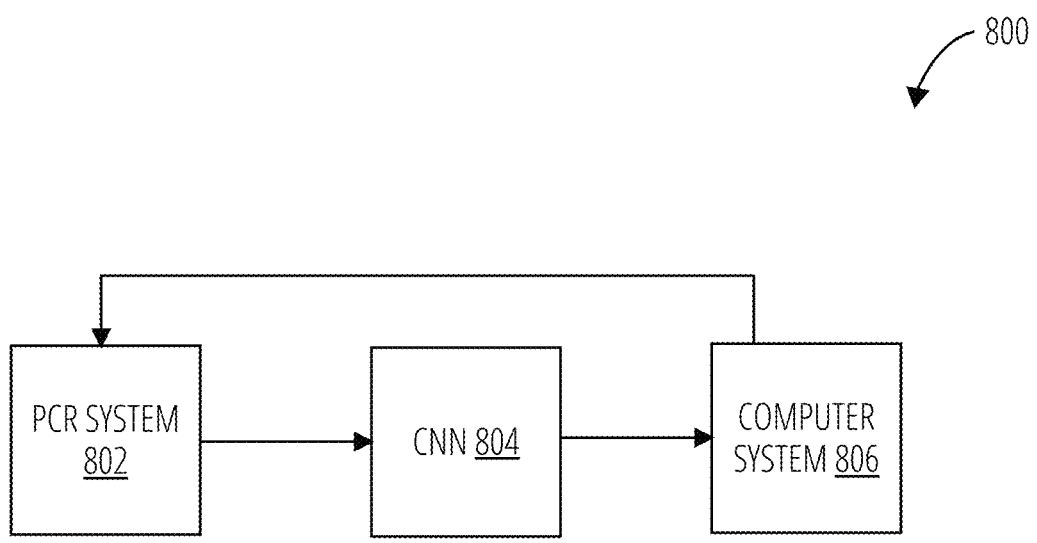
FIG. 8 illustrates a PCR quality control system 800 in accordance with one embodiment.

Referring to FIG. 8, a PCR quality control system 800 comprises a PCR system 802, a CNN 804, and a computer system 806. The PCR system 802 generates the QC images and sends those to the CNN 804. The CNN 804 may be an embodiment of the neural network 700 described above. The CNN 804 determines whether the QC image passes or fails. The result is sent to the computer system 806. The result may include whether the QC images passed or failed, which subarray failed, and by which failure mode. The computer system 806 may display the result to a user, store the result, perform addition transformations of the result, and control the PCR system 802 or set process parameters for improving the manufacture of the reaction plate array. The computer system 806 may also alter the PCR system 802 based on the result, such as stopping operation of a PCR system 802 that provides a failure result or correcting the PCR system 802 in the event of a failure. The PCR system 802 may generate a series of QC images, each at a different time. These QC images may be sent to the CNN 804 in series. For each image, the CNN 804 provides a result to the computer system 806.

Figure 9:
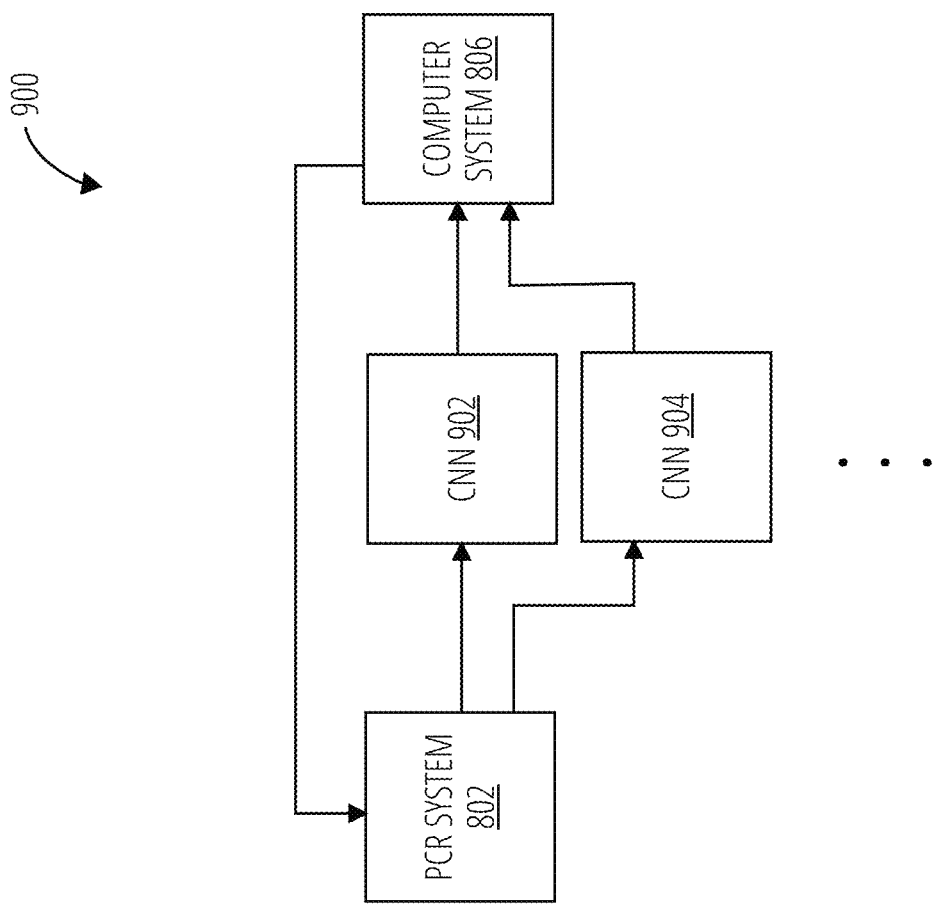
FIG. 9 illustrates a PCR quality control system 900 in accordance with one embodiment.

Referring to FIG. 9, a PCR quality control system 900 comprises a PCR system 802, a computer system 806, a CNN 902, and a CNN 904. The PCR quality control system 900 may operate similarly to the PCR quality control system 800. However, the PCR quality control system 900 may initialized multiple CNNs (the CNN 902, the CNN 904, etc.). Each CNN is then utilized on one of the subarray. Some QC images comprise 48 subarrays, and 48 CNNs may be operated. The computer system 806 may then combine the result from each of the CNNs. The result may include whether one subarray has a failed condition, which subarrays have the failed condition, and by which condition did each subarray fail.

Figure 10:
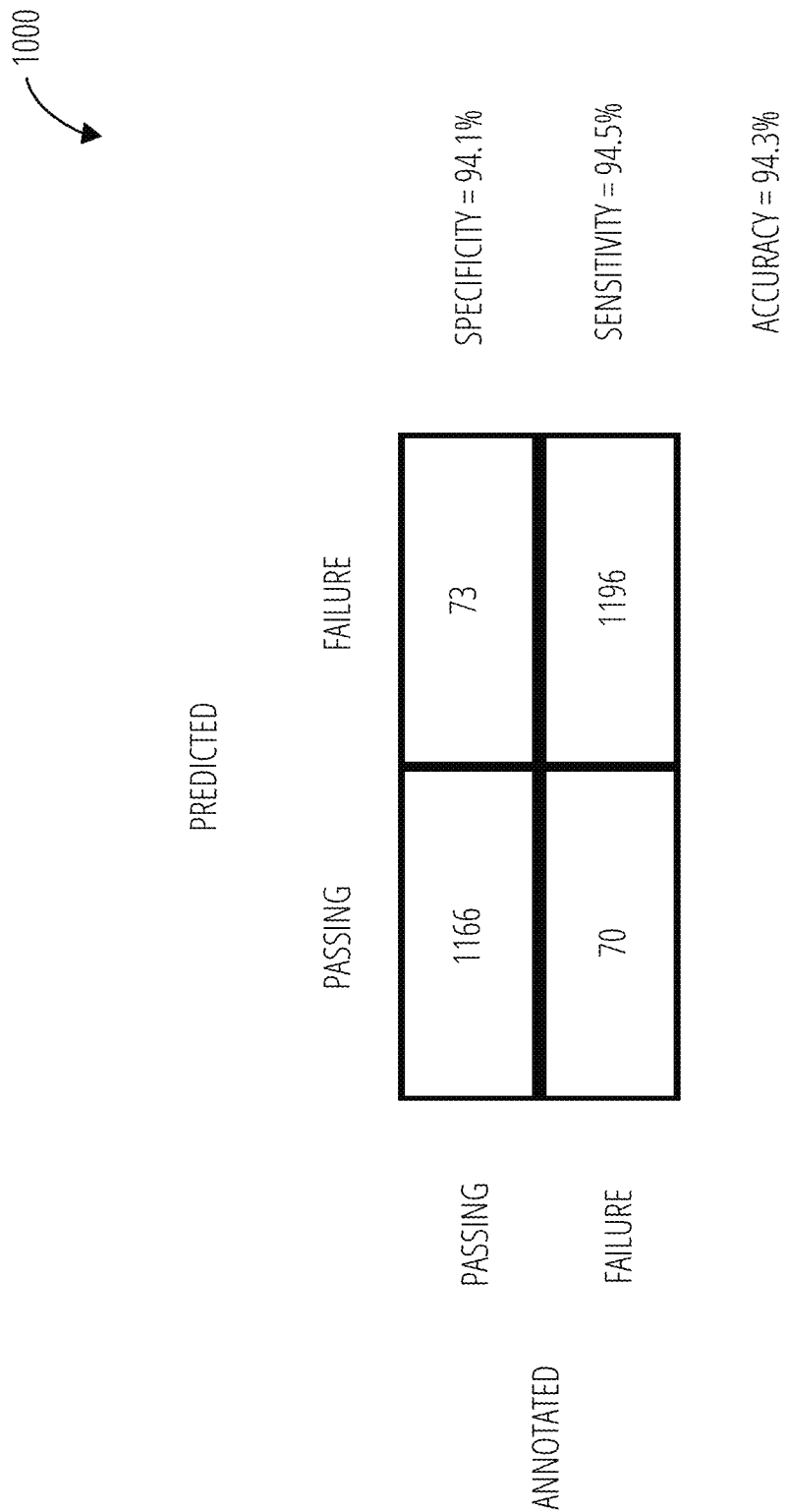
FIG. 10 illustrates a validation results 1000 in accordance with one embodiment.

Referring to FIG. 10, a validation results 1000 is depicted. The rows represent the annotated classification and the columns represent the prediction from the selected network. The top left box is when the annotated label is passing and the predicted classification is passing. For the given test, there were 1166 such results. The top right box is when the annotated label is passing and the predicted classification is failure. For the given test, there were 73 such results. The bottom left box is when the annotated label is failure and the predicted classification is passing. For the given test, there were 70 such results. The bottom right box is when the annotated label is failure and the predicted classification is failure. For the given test, there were 1196 such results. The resulting sensitivity (True positive/Annotated positives) is 94.1%. The resulting specificity (True negative/Annotated negatives) is 94.5%. The resulting accuracy ((True Positive+True Negatives)/Total population) is 94.3%.

Referring to FIG. 11, validation results 1100 are depicted. The validation results 1100 compares the annotated classification to the predicted classification. The classifications include passing and five failure modes: bright ROX, ROX spotting, ROX stripping, stop point bridging, and reformatting.

Figure 12:
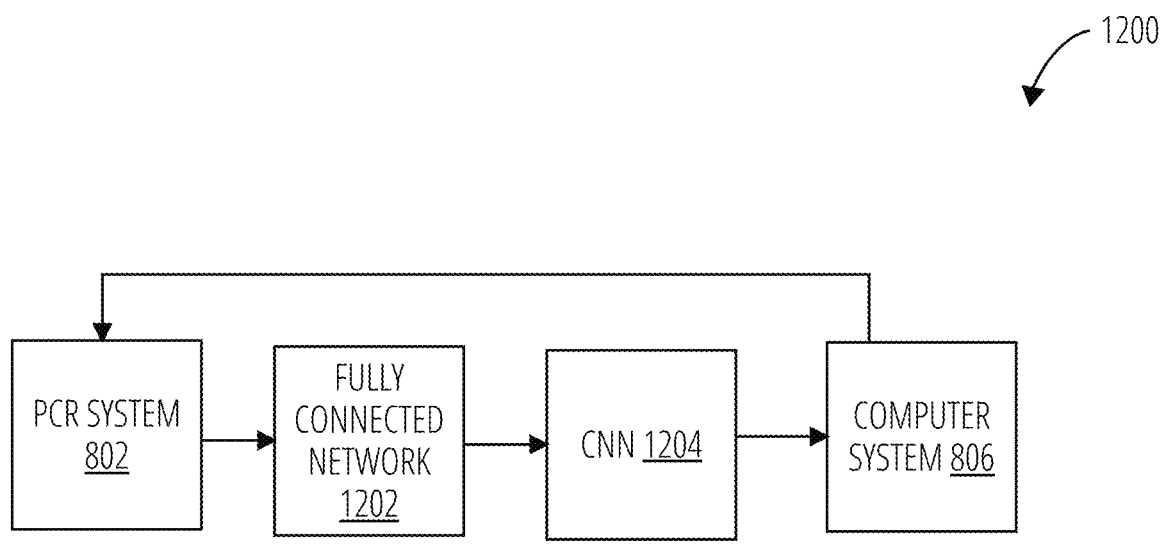
FIG. 12 illustrates a PCR quality control system 1200 in accordance with one embodiment.

Referring to FIG. 12, a PCR quality control system 1200 comprises a PCR system 802, a computer system 806, a fully connected network 1202, and a CNN 1204. The PCR system 802 generates the QC images and sends those to the fully connected network 1202. The fully connected network 1202 may comprise fully connected layers with one or more hidden layers. Unsupervised learning such as auto-encoders may be applied on QC images to learn simple or complex features, which are then used as the input for CNN 1204 or other fully connected networks to classify the QC images to passing and different failure modes. The CNN 1204 may be an embodiment of the neural network 700 described above. The CNN 1204 determines whether the QC image passes or fails. The result is sent to the computer system 806. The result may include whether the QC images passed or failed, which subarray failed, and by which failure mode. The computer system 806 may display the result to a user, store the result, perform addition transformations of the result, adjust future manufacturing parameters for the reaction plate array, and control the PCR system 802. The computer system 806 may also alter the PCR system 802 based on the result, such as stopping operation of a PCR system 802 that provides a failure result or correcting the PCR system 802 in the event of a failure. The PCR system 802 may generate a series of QC images, each at a different time. These QC images may be sent to the CNN 1204 in series. For each image, the CNN 1204 provides a result to the computer system 806. The PCR quality control system 1200 may also utilize multiple CNN 1204, similar to that depicted in FIG. 9, each CNN 1204 receiving a subarray. Furthermore, multiple fully connected network 1202 may be initialized, each receiving the subarray. The output of the fully connected network 1202 for each subarray may be sent to a CNN 1204.

Figure 13:
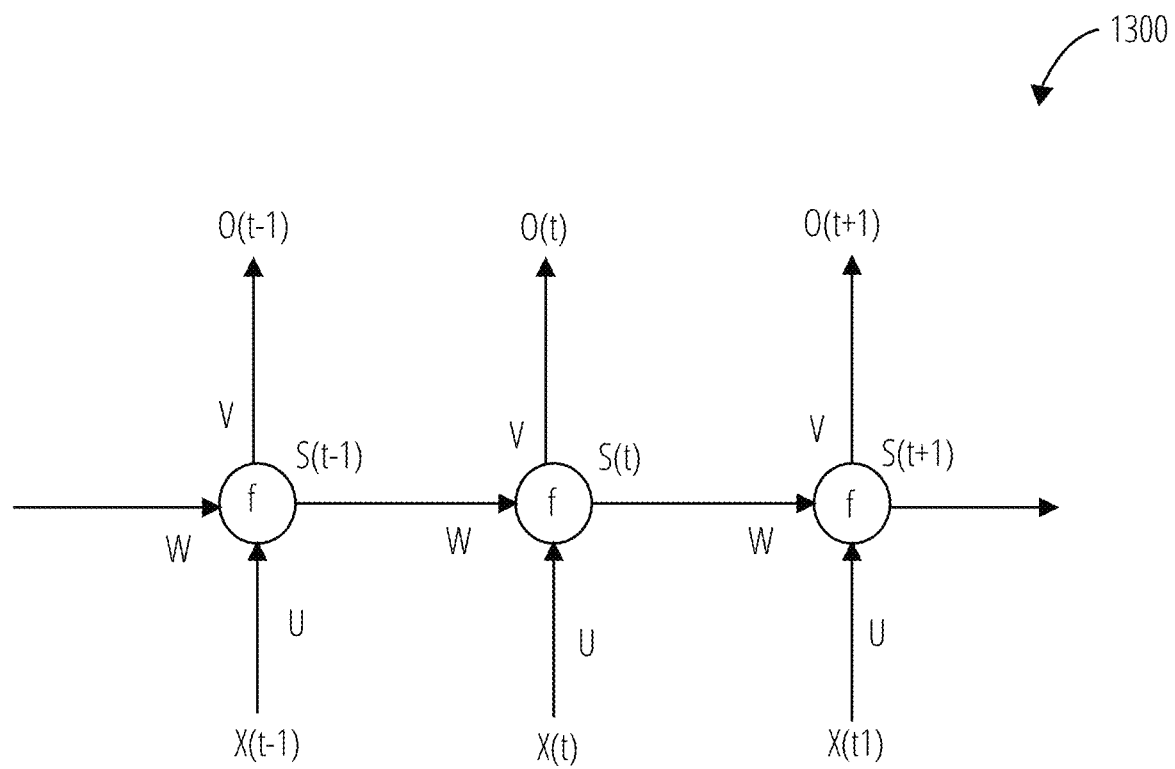
FIG. 13 illustrates a recurrent neural network 1300 in accordance with one embodiment.

FIG. 13 illustrates a recurrent neural network 1300 (RNN). Variable x[t] is the input at stage t. For example, x[1] could be a one-hot vector selecting a particular element in a sequence. Variable s[t] is the hidden state at stage t. It's the "memory" of the network. The variable s[t] is calculated based on the previous hidden state and the input at the current stage: $s[t]=f(Ux[t]+Ws[t-1])$. The activation function f usually is a nonlinearity such as tanh or ReLU. The input s(−1), which is required to calculate the first hidden state, is typically initialized to all zeroes. Variable o[t] is the output at stage t. For example, the prediction may be a vector of probabilities across the vocabulary: $o[t]=softmax(Vs[t])$. The recurrent neural network 1300 may be used to look at the evolution of the QC images over the course of the PCR reaction. One or multiple CNNs could input to the recurrent neural network 1300 (or be multiple RNNs, such as one per CNN), and the recurrent neural network 1300 outputs classification predictions based on how the CNN image classifications evolve over time. The CNN may have a modified output layer, such that the CNN does not predict the pass/fail, but sends a set of classification features as an input to the recurrent neural network 1300. The features may, for example, be the results of the second fully connected layer. If multiple RNNs are used (e.g., one per CNN), the analytic system may utilize a multilayer perceptron (a general purpose ANN) to combine the RNN predictions into a final prediction of failure mode.

Figure 14:
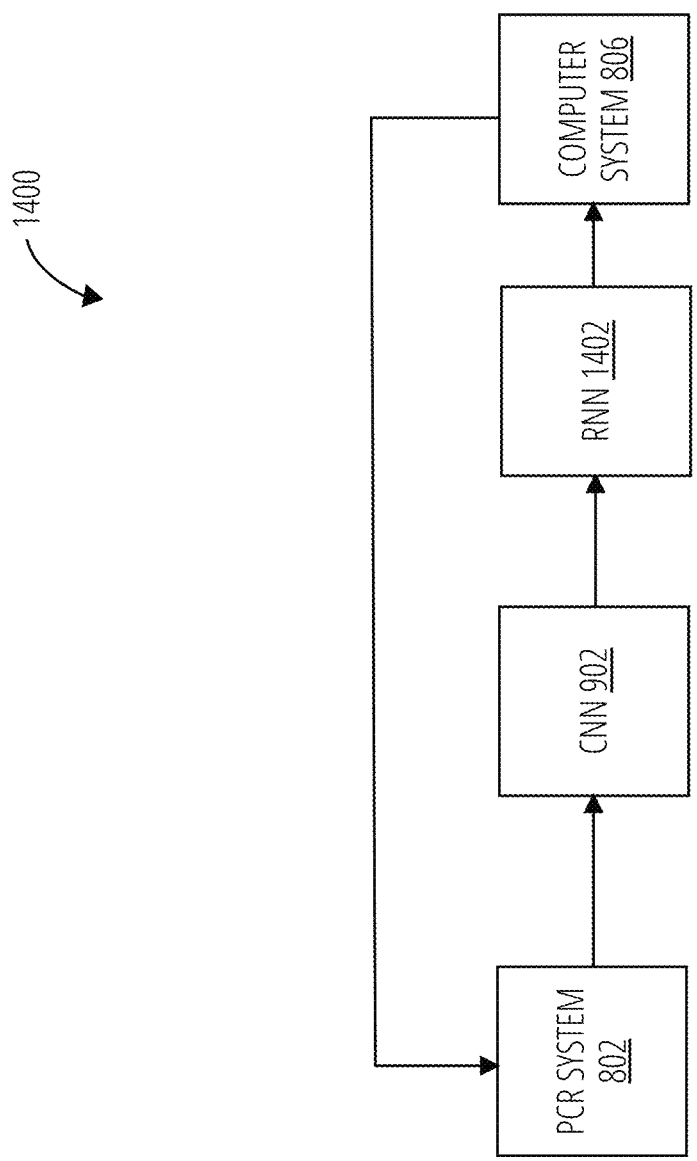
FIG. 14 illustrates a PCR quality control system 1400 in accordance with one embodiment.

Referring to FIG. 14, a PCR quality control system 1400 comprises a PCR system 802, a computer system 806, a CNN 902, and an RNN 1402. The PCR system 802 sends a series of QC images to the CNN 902. The series is based on a periodic sampling a reaction plate. Each image then has the CNN 902 applied to determine a classification or features (e.g., does not apply the final fully connected output layer). This is then sent to the RNN 1402. The RNN 1402 receives the series of classifications or features. The RNN 1402 then determines an output, such as that the PCR system 802 has failed or the PCR system 802 may fail due to the changes in the QC images determined by the RNN 1402. The RNN 1402 may also determine the failure mode. The computer system 806 may display the result to a user, store the result, perform addition transformations of the result, and control the PCR system 802. The computer system 806 may also alter the PCR system 802 based on the result, such as stopping operation of a PCR system 802 that provides a failure result or correcting the PCR system 802 in the event of a failure.

Figure 15:
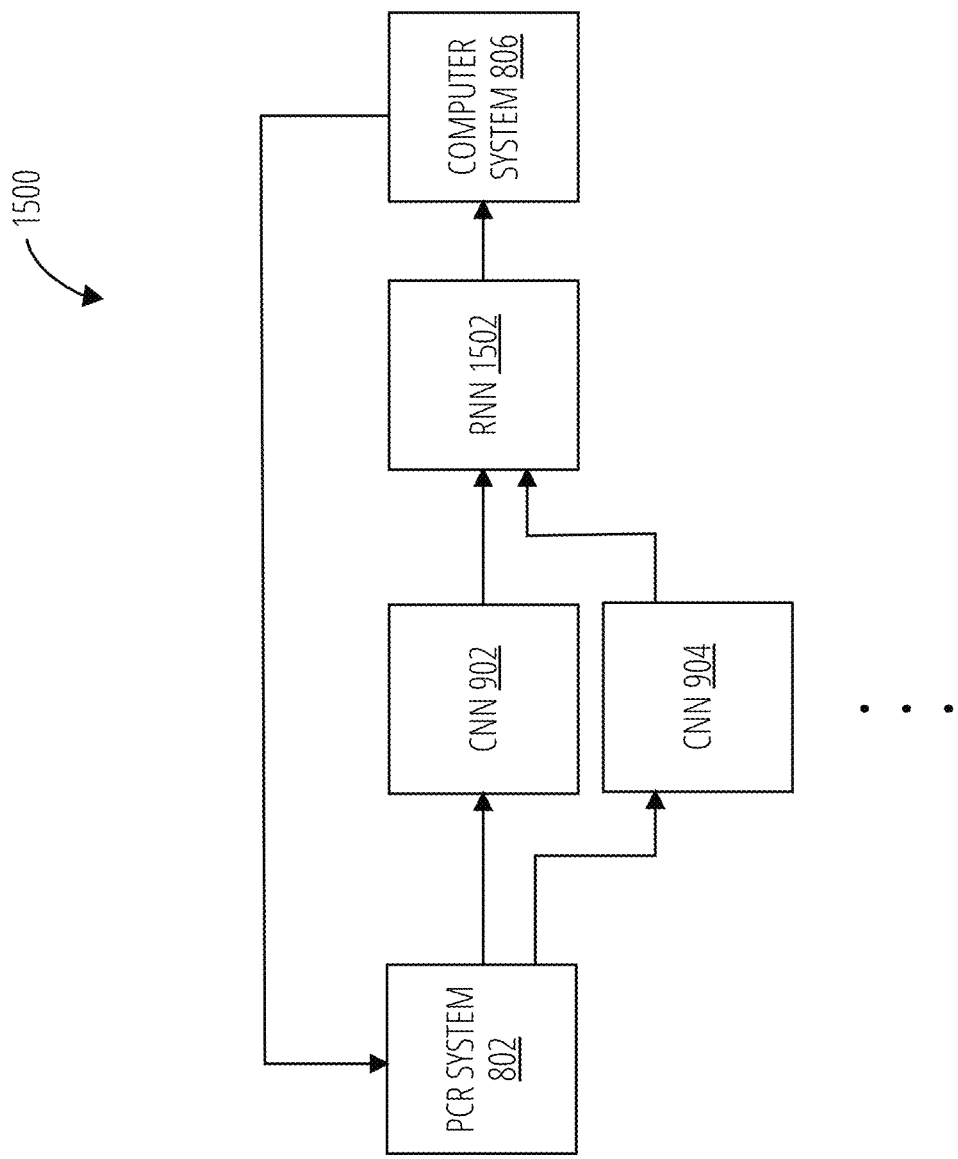
FIG. 15 illustrates a PCR quality control system 1500 in accordance with one embodiment.

Referring to FIG. 15, a PCR quality control system 1500 comprises a PCR system 802, a computer system 806, a CNN 902, a CNN 904, and an RNN 1502. The PCR system 802 sends a series of QC images to the CNN 902 and the CNN 904. The CNN 902, the CNN 904, and other CNNs may receive a subarray of the QC image in series. The series is based on a periodic sampling a reaction plate. Each image then has the CNN applied to determine a classification or features for the subarray (e.g., does not apply the final fully connected output layer). This is then sent to the RNN 1502. The RNN 1502 may also be multiple RNN in parallel, one for each subarray. The RNN 1502 receives the series of classifications or features. The RNN 1502 then determines an output, such as that the PCR system 802 has failed or the PCR system 802 may fail due to the changes in the QC images determined by the RNN 1502. The RNN 1502 may also determine the failure mode. The computer system 806 may display the result to a user, store the result, perform addition transformations of the result, and control the PCR system 802. The computer system 806 may also alter the PCR system 802 based on the result, such as stopping operation of a PCR system 802 that provides a failure result or correcting the PCR system 802 in the event of a failure.

Figure 16:
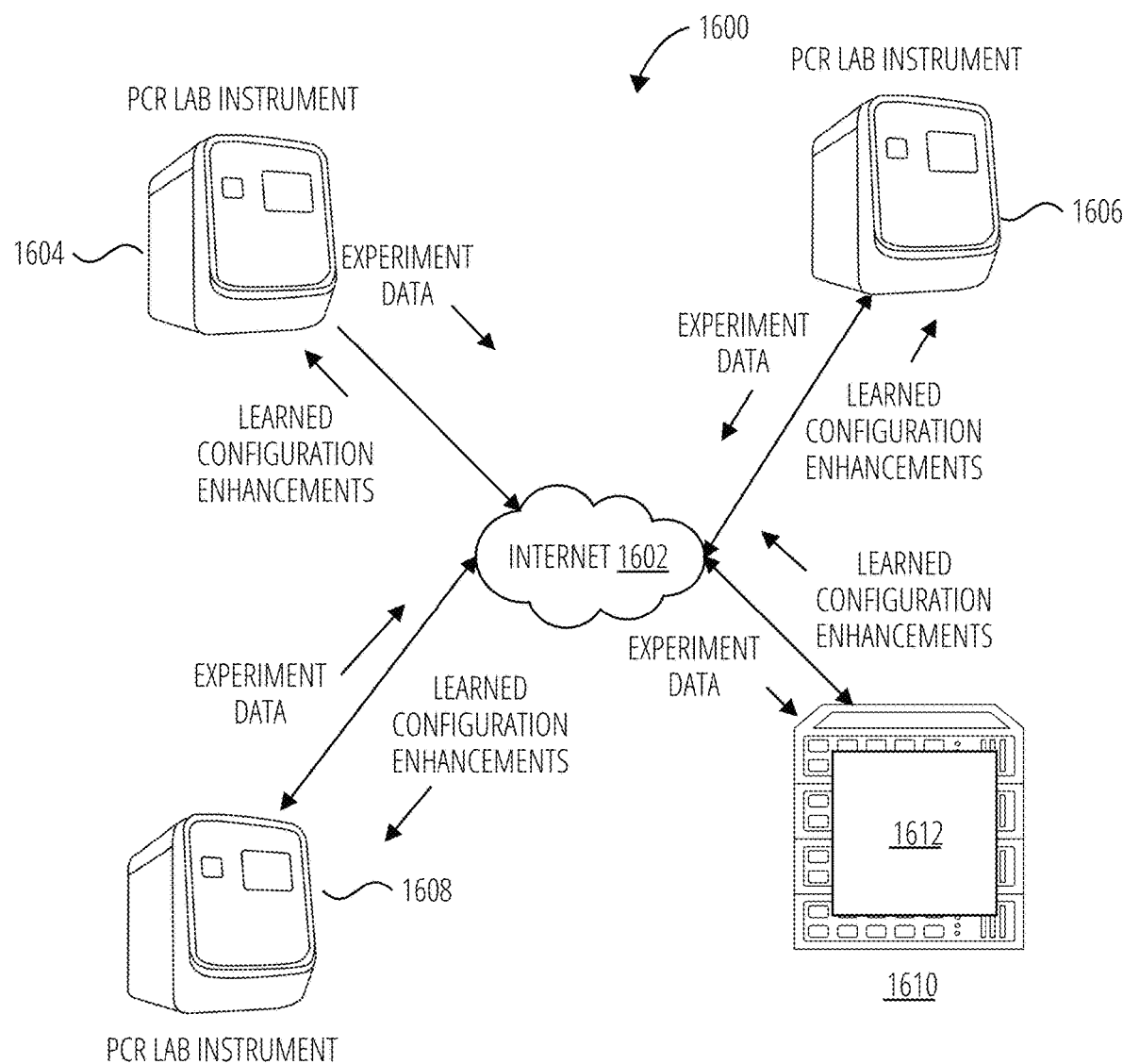
FIG. 16 illustrates a cloud learning and control system 1600 in accordance with one embodiment.

FIG. 16 illustrates a cloud learning and control system 1600 in accordance with one embodiment. The cloud learning and control system 1600 comprises a cloud analytic system 1610 that comprises a learning system 1612, for example one or more of the embodiments disclosed herein. The experimental data from a number of PCR runs or other experiments (e.g., PCR lab instrument 1604, PCR lab instrument 1606, and PCR lab instrument 1608) are monitored over the Internet 1602 or other network by the cloud analytic system 1610. The cloud analytic system 1610 processes the experimental data and provides learned configuration parameters as feedback to adjust the configuration settings PCR instruments for the current or future experiments.

Figure 17:
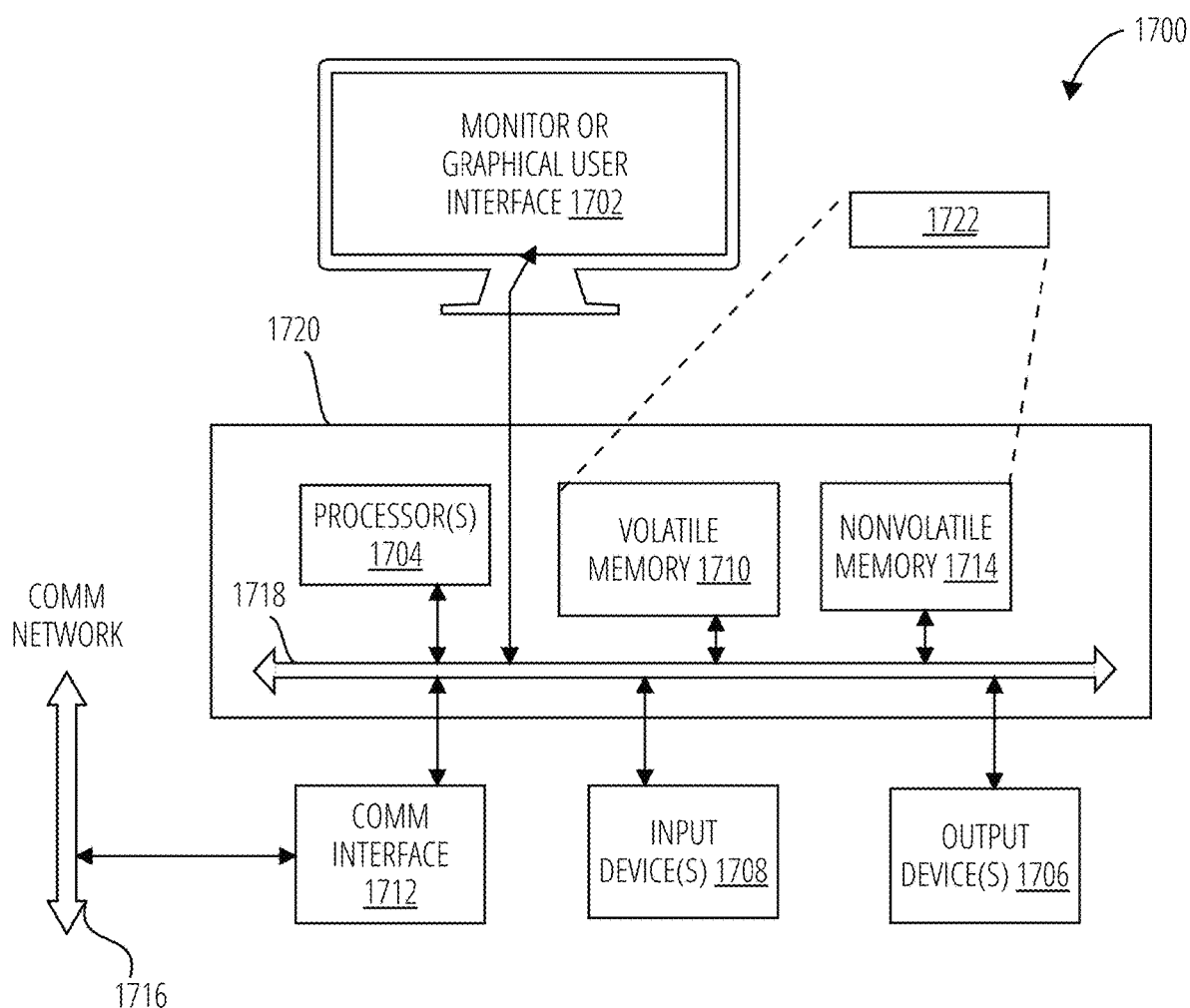
FIG. 17 is an example block diagram of a computing device 1700 that may incorporate embodiments of the present invention.

FIG. 17 is an example block diagram of a computing device 1700 that may incorporate embodiments of the present invention. FIG. 17 is merely illustrative of a machine system to carry out aspects of the technical processes described herein, and does not limit the scope of the claims. One of ordinary skill in the art would recognize other variations, modifications, and alternatives. In one embodiment, the computing device 1700 typically includes a monitor or graphical user interface 1702, a data processing system 1720, a communication network interface 1712, input device(s) 1708, output device(s) 1706, and the like.

As depicted in FIG. 17, the data processing system 1720 may include one or more processor(s) 1704 that communicate with a number of peripheral devices via a bus subsystem 1718. These peripheral devices may include input device(s) 1708, output device(s) 1706, communication network interface 1712, and a storage subsystem, such as a volatile memory 1710 and a nonvolatile memory 1714.

The volatile memory 1710 and/or the nonvolatile memory 1714 may store computer-executable instructions and thus forming logic 1722 that when applied to and executed by the processor(s) 1704 implement embodiments of the processes and neural networks disclosed herein.

The input device(s) 1708 include devices and mechanisms for inputting information to the data processing system 1720. These may include a keyboard, a keypad, a touch screen incorporated into the monitor or graphical user interface 1702, audio input devices such as voice recognition systems, microphones, and other types of input devices. In various embodiments, the input device(s) 1708 may be embodied as a computer mouse, a trackball, a track pad, a joystick, wireless remote, drawing tablet, voice command system, eye tracking system, and the like. The input device(s) 1708 typically allow a user to select objects, icons, control areas, text and the like that appear on the monitor or graphical user interface 1702 via a command such as a click of a button or the like.

The output device(s) 1706 include devices and mechanisms for outputting information from the data processing system 1720. These may include the monitor or graphical user interface 1702, speakers, printers, infrared LEDs, and so on as well understood in the art.

The communication network interface 1712 provides an interface to communication networks (e.g., communication network 1716) and devices external to the data processing system 1720. The communication network interface 1712 may serve as an interface for receiving data from and transmitting data to other systems. Embodiments of the communication network interface 1712 may include an Ethernet interface, a modem (telephone, satellite, cable, ISDN), (asynchronous) digital subscriber line (DSL), FireWire, USB, a wireless communication interface such as Bluetooth or Wi-Fi, a near field communication wireless interface, a cellular interface, and the like.

The communication network interface 1712 may be coupled to the communication network 1716 via an antenna, a cable, or the like. In some embodiments, the communication network interface 1712 may be physically integrated on a circuit board of the data processing system 1720, or in some cases may be implemented in software or firmware, such as "soft modems", or the like.

The computing device 1700 may include logic that enables communications over a network using protocols such as HTTP, TCP/IP, RTP/RTSP, IPX, UDP and the like.

The volatile memory 1710 and the nonvolatile memory 1714 are examples of tangible media configured to store computer readable data and instructions to implement various embodiments of the processes described herein. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), battery-backed volatile memories, networked storage devices, and the like. The volatile memory 1710 and the nonvolatile memory 1714 may be configured to store the basic programming and data constructs that provide the functionality of the disclosed processes and other embodiments thereof that fall within the scope of the present invention.

Logic 1722 that implements embodiments of the present invention may be embodied by the volatile memory 1710 and/or the nonvolatile memory 1714. Instructions of said logic 1722 may be read from the volatile memory 1710 and/or nonvolatile memory 1714 and executed by the processor(s) 1704. The volatile memory 1710 and the nonvolatile memory 1714 may also provide a repository for storing data used by the logic 1722.

The volatile memory 1710 and the nonvolatile memory 1714 may include a number of memories including a main random-access memory (RAM) for storage of instructions and data during program execution and a read only memory (ROM) in which read-only non-transitory instructions are stored. The volatile memory 1710 and the nonvolatile memory 1714 may include a file storage subsystem providing persistent (non-volatile) storage for program and data files. The volatile memory 1710 and the nonvolatile memory 1714 may include removable storage systems, such as removable flash memory.

The bus subsystem 1718 provides a mechanism for enabling the various components and subsystems of data processing system 1720 communicate with each other as intended. Although the communication network interface 1712 is depicted schematically as a single bus, some embodiments of the bus subsystem 1718 may utilize multiple distinct busses.

It will be readily apparent to one of ordinary skill in the art that the computing device 1700 may be a device such as a smartphone, a desktop computer, a laptop computer, a rack-mounted computer system, a computer server, or a tablet computer device. As commonly known in the art, the computing device 1700 may be implemented as a collection of multiple networked computing devices. Further, the computing device 1700 will typically include operating system logic (not illustrated) the types and nature of which are well known in the art.

Additional Terminology and Interpretation

Terms used herein should be accorded their ordinary meaning in the relevant arts, or the meaning indicated by their use in context, but if an express definition is provided, that meaning controls.

"Support Vector Machine" refers to supervised learning models with associated learning algorithms that analyze data used for classification and regression analysis. Given a set of training examples, each marked as belonging to one or the other of two categories, an SVM training algorithm builds a model that assigns new examples to one category or the other, making it a non-probabilistic binary linear classifier. An SVM model is a representation of the examples as points in space, mapped so that the examples of the separate categories are divided by a clear gap that is as wide as possible. New examples are then mapped into that same space and predicted to belong to a category based on which side of the gap they fall. In addition to performing linear classification, SVMs can efficiently perform a non-linear classification using what is called the kernel trick, implicitly mapping their inputs into high-dimensional feature spaces.

"Kernel" refers to kernel functions, which operate in a high-dimensional, implicit feature space without ever computing the coordinates of the data in that space, but rather by simply computing the inner products between the projections of all pairs of data in the feature space. This operation is often computationally cheaper than the explicit computation of the coordinates. When used with SVMs, this approach is called the "kernel trick".

"ReLU" refers to a rectifier function, an activation function defined as the positive part of ints input. It is also known as a ramp function and is analogous to half-wave rectification in electrical signal theory. ReLu is a popular activation function in deep neural networks.

"Loss function" refers to also referred to as the cost function or error function (not to be confused with the Gauss error function), is a function that maps values of one or more variables onto a real number intuitively representing some "cost" associated with those values.

"Hyperbolic tangent function" refers to a function of the form tanh(x)=sinh(x)/cosh(x). The tanh function is a popular activation function in artificial neural networks. Like the sigmoid, the tanh function is also sigmoidal ("s"-shaped), but instead outputs values that range (−1, 1). Thus strongly negative inputs to the tanh will map to negative outputs. Additionally, only zero-valued inputs are mapped to near-zero outputs. These properties make the network less likely to get "stuck" during training.

"Sigmoid function" refers to a function of the form f(x)=1/(exp(−x)). The sigmoid function is used as an activation function in artificial neural networks. It has the property of mapping a wide range of input values to the range 0-1, or sometimes −1 to 1.

"Backpropagation" refers to an algorithm used in artificial neural networks to calculate a gradient that is needed in the calculation of the weights to be used in the network. It is commonly used to train deep neural networks, a term referring to neural networks with more than one hidden layer. For backpropagation, the loss function calculates the difference between the network output and its expected output, after a case propagates through the network.

"Softmax function" refers to a function of the form f(xi)=exp(xi)/sum(exp(x)) where the sum is taken over a set of x. Softmax is used at different layers (often at the output layer) of artificial neural networks to predict classifications for inputs to those layers. The Softmax function calculates the probabilities distribution of the event xi over 'n' different events. In general sense, this function calculates the probabilities of each target class over all possible target classes. The calculated probabilities are helpful for predicting that the target class is represented in the inputs. The main advantage of using Softmax is the output probabilities range. The range will 0 to 1, and the sum of all the probabilities will be equal to one. If the Softmax function used for multi-classification model it returns the probabilities of each class and the target class will have the high probability. The formula computes the exponential (e-power) of the given input value and the sum of exponential values of all the values in the inputs. Then the ratio of the exponential of the input value and the sum of exponential values is the output of the Softmax function.

"CTC loss function" refers to connectionist temporal classification, a type of neural network output and associated scoring function, for training recurrent neural networks (RNNs) such as LSTM networks to tackle sequence problems where the timing is variable. A CTC network has a continuous output (e.g. Softmax), which is fitted through training to model the probability of a label. CTC does not attempt to learn boundaries and timings: Label sequences are considered equivalent if they differ only in alignment, ignoring blanks. Equivalent label sequences can occur in many ways—which makes scoring a non-trivial task. Fortunately there is an efficient forward—backward algorithm for that. CTC scores can then be used with the backpropagation algorithm to update the neural network weights. Alternative approaches to a CTC-fitted neural network include a hidden Markov model (HMM).

"Gated Recurrent Unit (GRU)" refers to are a gating mechanism in recurrent neural networks. GRUs may exhibit better performance on smaller datasets than do LSTMs. They have fewer parameters than LSTM, as they lack an output gate.

"Beam search" refers to a heuristic search algorithm that explores a graph by expanding the most promising node in a limited set. Beam search is an optimization of best-first search that reduces its memory requirements. Best-first search is a graph search which orders all partial solutions (states) according to some heuristic. But in beam search, only a predetermined number of best partial solutions are kept as candidates. It is thus a greedy algorithm. Beam search uses breadth-first search to build its search tree. At each level of the tree, it generates all successors of the states at the current level, sorting them in increasing order of heuristic cost. However, it only stores a predetermined number, β, of best states at each level (called the beam width). Only those states are expanded next. The greater the beam width, the fewer states are pruned. With an infinite beam width, no states are pruned and beam search is identical to breadth-first search. The beam width bounds the memory required to perform the search. Since a goal state could potentially be pruned, beam search sacrifices completeness (the guarantee that an algorithm will terminate with a solution, if one exists). Beam search is not optimal (that is, there is no guarantee that it will find the best solution). In general, beam search returns the first solution found. Beam search for machine translation is a different case: once reaching the configured maximum search depth (i.e. translation length), the algorithm will evaluate the solutions found during search at various depths and return the best one (the one with the highest probability). The beam width can either be fixed or variable. One approach that uses a variable beam width starts with the width at a minimum. If no solution is found, the beam is widened and the procedure is repeated.

"Adam optimizer" refers to an optimization algorithm that can used instead of the classical stochastic gradient descent procedure to update network weights iterative based in training data. Stochastic gradient descent maintains a single learning rate (termed alpha) for all weight updates and the learning rate does not change during training. A learning rate is maintained for each network weight (parameter) and separately adapted as learning unfolds. Adam as combining the advantages of two other extensions of stochastic gradient descent. Specifically, Adaptive Gradient Algorithm (Ada-Grad) that maintains a per-parameter learning rate that improves performance on problems with sparse gradients (e.g. natural language and computer vision problems), and Root Mean Square Propagation (RMSProp) that also maintains per-parameter learning rates that are adapted based on the average of recent magnitudes of the gradients for the weight (e.g. how quickly it is changing). This means the algorithm does well on online and non-stationary problems (e.g. noisy). Adam realizes the benefits of both AdaGrad and RMSProp. Instead of adapting the parameter learning rates based on the average first moment (the mean) as in RMSProp, Adam also makes use of the average of the second moments of the gradients (the uncentered variance). Specifically, the algorithm calculates an exponential moving average of the gradient and the squared gradient, and the parameters beta1 and beta2 control the decay rates of these moving averages. The initial value of the moving averages and beta1 and beta2 values close to 1.0 (recommended) result in a bias of moment estimates towards zero. This bias is overcome by first calculating the biased estimates before then calculating bias-corrected estimates.

"Assay" refers to in a PCR reaction mix, two target-specific primers or two primers and a probe used to amplify a target.

"Forward primer" refers to Oligonucleotide that flanks the 5' end of the amplicon. The reverse primer and the forward primer are used together in PCR reactions to amplify the target.

"Diluent" refers to A reagent used to dilute a sample or standard before it is added to the PCR reaction.

"Data collection" refers to During the instrument run, a process in which an instrument detects fluorescence data from each well of the reaction plate. The instrument transforms the signal to electronic data and saves the data in the experiment file.

"ROX dye" refers to an inert dye, whose fluorescence does not change during the reaction, and may be added to quantitative, real-time PCR reactions to normalize the well-to-well differences that may occur due to artifacts such as pipetting errors or instrument limitations. ROX Passive Reference Dye is composed of a 25 µM solution of 5-carboxy-X-rhodamine in 10 mM Tris-HCl (pH 8.6), 0.1 mM EDTA, and 0.01% Tween™-20. Although many instruments require use of the dye at final concentrations of 500 nM, newer instruments with optimized filter sets require use at 50 nM.

"Reference dye" refers to see ROX dye.

"Passive reference" refers to a dye that produces fluorescence signal independent of PCR amplification, and that is added to each reaction at a constant concentration. Because the passive reference signal should be consistent across all wells, it is used to normalize the reporter dye signal to account for non-PCR related fluorescence fluctuations caused by minor well to-well differences in volume. Normalization to the passive reference signal generally results in data with noticeably high precision among technical replicates.

"Reporter" refers to A fluorescent dye used to detect amplification. With TaqMan® reagents, the reporter dye is attached to the 5' end.

"Reverse primer" refers to an oligonucleotide that flanks the 3' end of the amplicon. The reverse primer and the forward primer are used together in PCR reactions to amplify the target.

"Circuitry" herein refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" herein refers to software logic embodied as processor-executable instructions stored in read-only memories or media.

"Hardware" herein refers to logic embodied as analog or digital circuitry.

"Logic" herein refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Software" herein refers to logic implemented as processor-executable instructions in a machine memory (e.g. read/write volatile or nonvolatile memory or media).

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Various logic functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

The invention claimed is:

1. A system comprising:
   a PCR system;
   a reaction array plate;
   a convolutional neural network (CNN) configured to receive a sequence of images of the reaction array plate in the PCR system;
   an output of the CNN coupled to a control for the reaction array plate; and
   at least one recurrent neural network (RNN) coupled to receive feature indications from the CNN, and to transform the feature indications into failure mode predictions.

2. The system of claim 1, wherein the control is a stop control.

3. The system of claim 1, further comprising:
a mapping function between through hole centers of the reaction array plate and arrays in layers of the CNN.

4. The system of claim 1, wherein the CNN lacks a final fully connected output layer.

5. The system of claim 1, comprising multiple RNNs, wherein predictions of multiple RNNs are combined by a perceptron into a final prediction of at least one failure mode.

6. The system of claim 1, the CNN further comprising:
an input layer comprising a 54×54 array;
a first convolution layer comprising 32 54×54 arrays; and
a second convolution layer comprising 64 18×18 arrays.

7. The system of claim 6, the CNN further comprising:
a first fully connected layer comprising 192 nodes;
a second fully connected layer coupled to the first fully connected layer and comprising 48 nodes; and
an output layer coupled to the second fully connected layer and generating a binary pass or a fail output signal.

8. The system of claim 7, the output layer further generating a prediction of a failure mode for the reaction array plate.

9. A method comprising:
operating a PCR system on a reaction array plate;
applying a sequence of images from a plurality of subarrays of the reaction array plate to a plurality of convolutional neural networks (CNNs) during operation of the PCR system on the reaction plate array;
operating the CNNs to generate failure mode predictions for the reaction plate based on the sequence of images; and
coupling an output of the CNNs to one or more of a setting for manufacture of the reaction array plate or to control the PCR system.

10. The method of claim 9, wherein the control is a stop control.

11. The method of claim 9, further comprising:
mapping through hole centers of the reaction array plate to different ones of the CNNs.

12. The method of claim 9, wherein one or more of the CNN lacks a final fully connected output layer.

13. The method of claim 12, further comprising coupling the output of the CNNs to at least one recurrent neural network (RNN) to receive feature indications from the CNNs, and to transform the feature indications into the failure mode predictions.

14. The method of claim 13, comprising multiple RNNs, wherein predictions of multiple RNNs are combined by a perceptron into a final prediction of at least one failure mode.

* * * * *